(12) United States Patent
Krishnan et al.

(10) Patent No.: US 9,404,123 B2
(45) Date of Patent: Aug. 2, 2016

(54) NUCLEIC ACID ASSEMBLY, VECTOR, CELL, METHODS AND KIT THEREOF

(71) Applicant: NATIONAL CENTRE FOR BIOLOGICAL SCIENCES, Bangalore (IN)

(72) Inventors: Yamuna Krishnan, Bangalore (IN); Souvik Modi, Bangalore (IN)

(73) Assignee: National Centre for Biological Sciences, Bangalore (IN)

( * ) Notice: Subject to any disclaimer, the term of this patent is extended or adjusted under 35 U.S.C. 154(b) by 0 days.

(21) Appl. No.: 14/351,400

(22) PCT Filed: Oct. 11, 2012

(86) PCT No.: PCT/IB2012/055515
§ 371 (c)(1),
(2) Date: Apr. 11, 2014

(87) PCT Pub. No.: WO2013/054286
PCT Pub. Date: Apr. 18, 2013

(65) Prior Publication Data
US 2014/0335568 A1    Nov. 13, 2014

(30) Foreign Application Priority Data

Oct. 12, 2011 (IN) .......................... 3252/CHE/2011

(51) Int. Cl.
| | | |
|---|---|---|
| C07H 21/02 | (2006.01) | |
| C07H 21/04 | (2006.01) | |
| A61K 48/00 | (2006.01) | |
| C12N 15/85 | (2006.01) | |
| C07K 16/44 | (2006.01) | |
| C12N 15/113 | (2010.01) | |

(52) U.S. Cl.
CPC ................ *C12N 15/85* (2013.01); *C07K 16/44* (2013.01); *C12N 15/113* (2013.01); *C07K 2317/34* (2013.01); *C07K 2317/565* (2013.01); *C07K 2317/622* (2013.01); *C07K 2317/82* (2013.01); *C07K 2317/92* (2013.01); *C07K 2319/00* (2013.01); *C12N 2810/85* (2013.01); *C12N 2810/859* (2013.01)

(58) Field of Classification Search
CPC .......................... C12N 15/113; C12N 2310/11
See application file for complete search history.

(56) References Cited

U.S. PATENT DOCUMENTS

| 8,216,850 B2 | 7/2012 | Krishnan et al. |
| 2005/0170348 A1 | 8/2005 | Sera |

FOREIGN PATENT DOCUMENTS

WO    WO-03/062447 A2    7/2003

OTHER PUBLICATIONS

Marschall, A.L.J., et al., "Targeting antibodies fo the cytoplasm," mAbs, Jan.-Feb. 2011, vol. 3, No. 1, pp. 3-16, Epub Jan 1, 2011, Table 2.
International Search Report and Written Opinion of the ISA, ISA/AU, mailed Feb. 13, 2013.
International Preliminary Report on Patentability (Chapter II), ISA/AU, issued Oct. 3, 2013.

*Primary Examiner* — Amy Bowman
(74) *Attorney, Agent, or Firm* — Harness, Dickey & Pierce, PLC

(57) ABSTRACT

The present disclosure relates to a nucleic acid assembly (NAA), comprising sensor domain and handle domain; an assembly interfaceable motif (AIM) sequence optionally along with intracellular targeting motif (ITM) sequence; and an AIM-NAA complex. It also relates to a vector comprising assembly interfaceable motif sequence optionally along with intracellular targeting motif sequence and a cell comprising the vector. Further, the instant disclosure also provides a method to obtain the nucleic acid assembly, method of intracellular targeting and kit thereof.

20 Claims, 15 Drawing Sheets
(14 of 15 Drawing Sheet(s) Filed in Color)

SEQ ID No. 23: Ic-myc  5'-CCC CA CCCT  CCCCA CCC TC CCC   ATA——
                         ||   | ||| | ||| |  ||    |||
SEQ ID No. 24:       3'-  GA   TGTGT GTG AG TGTTTTTAT——

SEQ ID No. 25: I³    5'-CCC TAA CCC TAA CCC TAA CCC ATA——
                        ||| | | ||| | | ||| | |||    |||
SEQ ID No. 26:       3'-T ATT GTG ATT GTG ATT GTT TAT——

SEQ ID No. 27: I^c3-c4   5'-CCCC TAA CCC  TAA CCCC TAACCC ATA——
                            |||| |   ||| | |  ||||    |||
SEQ ID No. 28:       3'-T ATT GTGTATT  GTGT ATTGTTTTAT——

SEQ ID No. 29: I⁴    5'-CCCC TAA CCCC TAA CCCC TAA CCCC ATA——
                        ||| | |  ||| | |  ||| |      |||
SEQ ID No. 30:       3'-TATT GTGT ATT GTGT ATT GTTT TAT——

(SEQ ID No. 13)
(SEQ ID No. 14)

SEQ ID No. 52: CCCTAGCCTCGAGAATTCACGACCGGTATGGAGCTGAGGCCCTGGTTGCTAT
GGGTGGTAGCAGCAACAGGAACCTTGGTCCTGCTAGCAGCTGATGCTCAGG
GCCAGAAGGTCTTACCAGTCGCCACCATGGTGAGCGGTGGATCTGGTAGCG
GCGGCGGCGGCTCTGGTGGTGGTAGATCTGGTCAGCCGGCCATGGCCGAGG
TGCAGCTGTTGGAGTCTGGGGGAGGCTTGGTACAGCCTGGGGGGTCCCTGA
GACTCTCCTGTGCAGCCTCTGGATTCACCTTTAGCAGCTATGCCATGAGCTG
GGTCCGCCAGGCTCCAGGGAAGGGGCTGGAGTGGGTCTCAACGATTACGAA
GAGGGGTGAGAGGACAAAGTACGCAGACTCCGTGAAGGGCCGGTTCACCA
TCTCCAGAGACAATTCCAAGAACACGCTGTATCTGCAAATGAACAGCCTGA
GAGCCGAGGACACGGCCGTATATTACTGTGCGAAAAGTACTCGTGCGTTTG
ACTACTGGGGCCAGGGAACCCTGGTCACCGTCTCGAGCGGTGGAGGCGGTT
CAGGCGGAGGTGGCAGCGGCGGTGGCGGGTCGACGGACATCCAGATGACCC
AGTCTCCATCCTCCCTGTCTGCATCTGTAGGAGACAGAGTCACCATCACTTG
CCGGGCAAGTCAGAGCATTAGCAGCTATTTAAATTGGTATCAGCAGAAACC
AGGGAAAGCCCCTAAGCTCCTGATCTATGGGGCATCCTATTTGCAAAGTGG
GGTCCCATCAAGGTTCAGTGGCAGTGGATCTGGGACAGATTTCACTCTCACC
ATCAGCAGTCTGCAACCTGAAGATTTTGCAACTTACTACTGTCAACAGACGC
GTTTTTCGCCTAATACGTTCGGCCAAGGGACCAAGGTGGAAATCAAACGGG
CGGCCGCACATCATCATCACCATCACGGGGCCGCAGAACAAAAACCCATCT
CAGAAGAGGATCTGAATGGGGCCGCAGGTGGGGATCTCCAGGTAGCAGTG
GCCGGCTGTGTTTTCCTGCTGATCAGCGTCCTCCTCCTGAGTGGGCTCACCT
GGCAGCGGTGTTCAGGCTTCAGCTTCCGGGGAGTGAAAGTGTACACCATGG
ACCGTGGCCTCATCTCCTACAAGGGGCTGCCTCCTGAGGCCTGGCAGGAGG

FIGURE 20(a)

AGTGCCCATCTGACTCAGAAGAGGATGAGGGCCGGGGTGAGAGGACCGAC
TGTCTATTTCTTTTCTAGATAAGAAAGGGG

Yellow: EcoRI site (Strat site of scFv-Furin gene)

SEQUENCE LISTING

```
<160> NUMBER OF SEQ ID NOS: 58

<210> SEQ ID NO 1
<211> LENGTH: 60
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(60)

<400> SEQUENCE: 1
```

```
cccctaaccc ctaaccccta accccatata tatcctagaa cgacagacaa acagtgagtc    60
```

<210> SEQ ID NO 2
<211> LENGTH: 72
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(72)

<400> SEQUENCE: 2

```
ccccccctaa ccccccctaa ccccccctaa cccccccata tatatcctag aacgacagac    60
aaacagtgag tc                                                         72
```

<210> SEQ ID NO 3
<211> LENGTH: 58
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(58)

<400> SEQUENCE: 3

```
cccctaaccc taaccctaa cccatatata tcctagaacg acagacaaac agtgagtc        58
```

<210> SEQ ID NO 4
<211> LENGTH: 57
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(57)

<400> SEQUENCE: 4

```
gactcactgt ttgtctgtcg ttctaggata tatattttgt tatgtgttat gtgttat        57
```

<210> SEQ ID NO 5
<211> LENGTH: 69
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(69)

<400> SEQUENCE: 5

```
ccctaaccct aaccctaacc catatatatc ctagaacgac agacaaacag tgagtccgca    60
ttgttacat                                                             69
```

<210> SEQ ID NO 6
<211> LENGTH: 67
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(67)

<400> SEQUENCE: 6

```
atgtaacaat gcggactcac tgtttgtctg tcgttctagg atatatattt gttagtgtta        60
gtgttat                                                                 67
```

<210> SEQ ID NO 7
<211> LENGTH: 57
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(57)

<400> SEQUENCE: 7

```
ccccaccctc cccaccctcc ccatatatat cctagaacga cagacaaaca gtgagtc         57
```

<210> SEQ ID NO 8
<211> LENGTH: 53
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(53)

<400> SEQUENCE: 8

```
gactcactgt ttgtctgtcg ttctaggata tatattttg tgagtgtgtg tag              53
```

<210> SEQ ID NO 9
<211> LENGTH: 60
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(60)

<400> SEQUENCE: 9

```
cccctaaccc ctaaccccta acccatata tatcctagaa cgacagacaa acagtgagtc       60
```

<210> SEQ ID NO 10
<211> LENGTH: 56
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(56)

<400> SEQUENCE: 10

```
ccctaacccct aacctaacc catatatatc ctagaacgac agacaaacag tgagtc          56
```

<210> SEQ ID NO 11
<211> LENGTH: 72
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(72)

<400> SEQUENCE: 11

```
cccccccctaa ccccccctaa cccccccta cccccccata tatatcctag aacgacagac      60
```

```
aaacagtgag tc                                                          72

<210> SEQ ID NO 12
<211> LENGTH: 57
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(57)

<400> SEQUENCE: 12
gactcactgt tgtctgtcg ttctaggata tatattttgt tatgtgttat gtgttat        57

<210> SEQ ID NO 13
<211> LENGTH: 39
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(39)

<400> SEQUENCE: 13
aaaagactca ctgtttgtct gtcgttctag gatatatat                           39

<210> SEQ ID NO 14
<211> LENGTH: 35
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(35)

<400> SEQUENCE: 14
atatatatcc tagaacgaca gacaaacagt gagtc                               35

<210> SEQ ID NO 15
<211> LENGTH: 13
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(13)

<400> SEQUENCE: 15
atatatatcc tag                                                        13

<210> SEQ ID NO 16
<211> LENGTH: 13
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(13)

<400> SEQUENCE: 16
cgacagacaa aca                                                        13

<210> SEQ ID NO 17
```

```
<211> LENGTH: 13
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(13)

<400> SEQUENCE: 17
cctagaacga cag                                                          13

<210> SEQ ID NO 18
<211> LENGTH: 48
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(48)

<400> SEQUENCE: 18
atatatatcc tagaacgaca gacaaacagt gagtccgcat tgttacat                    48

<210> SEQ ID NO 19
<211> LENGTH: 48
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(48)

<400> SEQUENCE: 19
atgtaacaat gcggactcac tgtttgtctg tcgttctagg atatatat                    48

<210> SEQ ID NO 20
<211> LENGTH: 20
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(20)

<400> SEQUENCE: 20
aggctttaaa taccggcatg                                                   20

<210> SEQ ID NO 21
<211> LENGTH: 20
<212> TYPE: DNA
<213> ORGANISM: Artificial Sequence
<220> FEATURE:
<223> OTHER INFORMATION: Nucleic Acid Assembly
<220> FEATURE:
<221> NAME/KEY: gene
<222> LOCATION: (1)..(20)

<400> SEQUENCE: 21
catgccggta tttaaagcct                                                   20

<210> SEQ ID NO 22
<211> LENGTH: 17
<212> TYPE: DNA
<213> ORGANISM: Artificial Sequence
<220> FEATURE:
```

<223> OTHER INFORMATION: Primer
<220> FEATURE:
<221> NAME/KEY: gene
<222> LOCATION: (1)..(17)

<400> SEQUENCE: 22
ctatgcggcc ccattca                                                     17

<210> SEQ ID NO 23
<211> LENGTH: 25
<212> TYPE: DNA
<213> ORGANISM: Artificial Sequence
<220> FEATURE:
<223> OTHER INFORMATION: Nucleic Acid

<400> SEQUENCE: 23
ccccaccctc cccaccctcc ccata                                            25

<210> SEQ ID NO 24
<211> LENGTH: 21
<212> TYPE: DNA
<213> ORGANISM: Artificial Sequence
<220> FEATURE:
<223> OTHER INFORMATION: Nucleic Acid

<400> SEQUENCE: 24
tatttttgtg agtgtgtgta g                                                21

<210> SEQ ID NO 25
<211> LENGTH: 24
<212> TYPE: DNA
<213> ORGANISM: Artificial Sequence
<220> FEATURE:
<223> OTHER INFORMATION: Nucleic Acid

<400> SEQUENCE: 25
ccctaaccct aaccctaacc cata                                             24

<210> SEQ ID NO 26
<211> LENGTH: 22
<212> TYPE: DNA
<213> ORGANISM: Artificial Sequence
<220> FEATURE:
<223> OTHER INFORMATION: Nucleic Acid

<400> SEQUENCE: 26
tatttgttag tgttagtgtt at                                               22

<210> SEQ ID NO 27
<211> LENGTH: 26
<212> TYPE: DNA
<213> ORGANISM: Artificial Sequence
<220> FEATURE:
<223> OTHER INFORMATION: Nucleic Acid

<400> SEQUENCE: 27
cccctaaccc taacccctaa cccata                                           26

<210> SEQ ID NO 28
<211> LENGTH: 25
<212> TYPE: DNA
<213> ORGANISM: Artificial Sequence
<220> FEATURE:
<223> OTHER INFORMATION: Nucleic Acid

<400> SEQUENCE: 28

```
tattttgtta tgtgttatgt gttat                                              25
```

<210> SEQ ID NO 29
<211> LENGTH: 28
<212> TYPE: DNA
<213> ORGANISM: Artificial Sequence
<220> FEATURE:
<223> OTHER INFORMATION: Nucleic Acid

<400> SEQUENCE: 29

```
cccctaaccc ctaacccta accccata                                            28
```

<210> SEQ ID NO 30
<211> LENGTH: 25
<212> TYPE: DNA
<213> ORGANISM: Artificial Sequence
<220> FEATURE:
<223> OTHER INFORMATION: Nucleic Acid

<400> SEQUENCE: 30

```
tattttgtta tgtgttatgt gttat                                              25
```

<210> SEQ ID NO 31
<211> LENGTH: 49
<212> TYPE: PRT
<213> ORGANISM: Artificial Sequence
<220> FEATURE:
<223> OTHER INFORMATION: F7/1-49 peptide

<400> SEQUENCE: 31

Ser Ile Ser Arg Lys Gly Arg Ser Thr Glu Tyr Ala Asp Tyr Cys Ala
1               5                   10                  15

Lys Ser Met Val Ala Phe Asp Tyr Lys Leu Leu Ile Tyr Ala Ala Ser
            20                  25                  30

Tyr Leu Gln Ser Cys Gln Gln Ala Leu Arg Arg Pro Leu Thr Phe Gly
        35                  40                  45

Gln

<210> SEQ ID NO 32
<211> LENGTH: 50
<212> TYPE: PRT
<213> ORGANISM: Artificial Sequence
<220> FEATURE:
<223> OTHER INFORMATION: G3/1-50 peptide

<400> SEQUENCE: 32

Ser Ile Ser Arg Lys Gly Arg Ser Thr Glu Tyr Ala Asp Tyr Cys Ala
1               5                   10                  15

Lys Ser Met Val Ala Phe Asp Tyr Trp Lys Leu Leu Ile Tyr Ala Ala
            20                  25                  30

Ser Tyr Leu Gln Ser Cys Gln Gln Ala Leu Arg Arg Pro Leu Thr Phe
        35                  40                  45

Gly Gln
    50

<210> SEQ ID NO 33
<211> LENGTH: 49
<212> TYPE: PRT
<213> ORGANISM: Artificial Sequence
<220> FEATURE:
<223> OTHER INFORMATION: C5/1-49 peptide

<400> SEQUENCE: 33

```
Ser Ile Ser Ala Glu Gly Lys Ala Thr Ser Tyr Ala Asp Cys Ala Lys
1               5                   10                  15

Ser Thr Arg Gly Phe Asp Tyr Lys Leu Leu Ile Tyr Gly Ala Ser Tyr
            20                  25                  30

Leu Gln Ser Cys Gln Gln Ala Arg Asn Leu Pro Arg Thr Phe Gly Gln
        35                  40                  45

Gly

<210> SEQ ID NO 34
<211> LENGTH: 46
<212> TYPE: PRT
<213> ORGANISM: Artificial Sequence
<220> FEATURE:
<223> OTHER INFORMATION: F10/1-46 peptide

<400> SEQUENCE: 34

Ser Ile Ser Ala Glu Gly Lys Glu Thr Glu Tyr Ala Cys Ala Lys Ser
1               5                   10                  15

Lys Arg Gly Phe Asp Tyr Leu Leu Ile Tyr Gly Ala Ser Tyr Leu Gln
            20                  25                  30

Ser Cys Gln Gln Gly Arg Asn Leu Pro Arg Thr Phe Gly Gln
        35                  40                  45

<210> SEQ ID NO 35
<211> LENGTH: 46
<212> TYPE: PRT
<213> ORGANISM: Artificial Sequence
<220> FEATURE:
<223> OTHER INFORMATION: C12/1-46 peptide

<400> SEQUENCE: 35

Ser Ile Ser Ala Lys Gly Arg Glu Thr Gln Tyr Ala Cys Ala Lys Ala
1               5                   10                  15

Lys Ser Thr Phe Asp Tyr Leu Leu Ile Tyr Ala Ala Ser Arg Leu Gln
            20                  25                  30

Ser Cys Gln Gln Gly Arg His Asn Pro Arg Thr Phe Gly Gln
        35                  40                  45

<210> SEQ ID NO 36
<211> LENGTH: 50
<212> TYPE: PRT
<213> ORGANISM: Artificial Sequence
<220> FEATURE:
<223> OTHER INFORMATION: C7/1-50 peptide

<400> SEQUENCE: 36

Ser Ile Ser Ala Lys Gly Arg Glu Thr Gln Tyr Ala Asp Ser Cys Ala
1               5                   10                  15

Lys Ala Lys Ser Thr Phe Asp Tyr Trp Lys Leu Leu Ile Tyr Ala Ala
            20                  25                  30

Ser Arg Leu Gln Ser Cys Gln Gln Gly Arg His Asn Pro Arg Thr Phe
        35                  40                  45

Gly Gln
    50

<210> SEQ ID NO 37
<211> LENGTH: 24
<212> TYPE: PRT
<213> ORGANISM: Artificial Sequence
<220> FEATURE:
<223> OTHER INFORMATION: E5/1-30 peptide
```

-continued

```
<400> SEQUENCE: 37

Phe Asp Tyr Leu Leu Ile Tyr Ala Ala Ser Arg Leu Gln Ser Gln Gln
1               5                   10                  15

Arg His Asn Pro Arg Thr Phe Gly
            20

<210> SEQ ID NO 38
<211> LENGTH: 48
<212> TYPE: PRT
<213> ORGANISM: Artificial Sequence
<220> FEATURE:
<223> OTHER INFORMATION: G2/1-48 peptide

<400> SEQUENCE: 38

Arg Ile Thr Pro Glu Gly Gln Arg Thr Ala Tyr Ala Asp Cys Ala Lys
1               5                   10                  15

Asp Asn Arg Thr Phe Asp Tyr Leu Leu Ile Tyr Ser Ala Ser Asn Leu
            20                  25                  30

Gln Ser Cys Gln Gln Thr Arg Asn Lys Pro Ser Thr Phe Gly Gln Gly
        35                  40                  45

<210> SEQ ID NO 39
<211> LENGTH: 46
<212> TYPE: PRT
<213> ORGANISM: Artificial Sequence
<220> FEATURE:
<223> OTHER INFORMATION: G5/1-46 peptide

<400> SEQUENCE: 39

Arg Ile Ser Pro Lys Gly His Glu Thr Gln Tyr Ala Asp Tyr Cys Ala
1               5                   10                  15

Lys Pro His Pro Thr Phe Asp Tyr Lys Leu Leu Ile Tyr Gly Ala Ser
            20                  25                  30

Trp Leu Gln Ser Cys Gln Gln Asn Arg Arg Ala Pro Thr Thr
        35                  40                  45

<210> SEQ ID NO 40
<211> LENGTH: 35
<212> TYPE: PRT
<213> ORGANISM: Artificial Sequence
<220> FEATURE:
<223> OTHER INFORMATION: D1/1-35 peptide

<400> SEQUENCE: 40

Cys Ala Lys Gly Thr Leu Ala Phe Asp Tyr Leu Leu Ile Tyr Ala Ala
1               5                   10                  15

Ser His Leu Gln Ser Cys Gln Gln Met Lys Arg Pro Ala Thr Phe
            20                  25                  30

Gly Gln Gly
        35

<210> SEQ ID NO 41
<211> LENGTH: 43
<212> TYPE: PRT
<213> ORGANISM: Artificial Sequence
<220> FEATURE:
<223> OTHER INFORMATION: C1/1-43 peptide

<400> SEQUENCE: 41

Thr Ile Thr Lys Lys Gly Glu Arg Thr Lys Tyr Ala Asp Cys Ala Lys
1               5                   10                  15

Ser Thr Arg Ala Phe Asp Tyr Ile Tyr Gly Ala Ser Tyr Leu Gln Ser
```

Cys Gln Gln Thr Arg Phe Ser Pro Asn Thr Phe
         35                  40

<210> SEQ ID NO 42
<211> LENGTH: 43
<212> TYPE: PRT
<213> ORGANISM: Artificial Sequence
<220> FEATURE:
<223> OTHER INFORMATION: G1/1-43 peptide

<400> SEQUENCE: 42

Thr Ile Thr Lys Lys Gly Glu Arg Thr Lys Tyr Ala Asp Cys Ala Lys
1               5                   10                  15

Ser Thr Arg Ala Phe Asp Tyr Ile Tyr Gly Ala Ser Tyr Leu Gln Ser
            20                  25                  30

Cys Gln Gln Thr Arg Phe Ser Pro Asn Thr Phe
         35                  40

<210> SEQ ID NO 43
<211> LENGTH: 45
<212> TYPE: PRT
<213> ORGANISM: Artificial Sequence
<220> FEATURE:
<223> OTHER INFORMATION: D7/1-45 peptide

<400> SEQUENCE: 43

Thr Ile Thr Lys Lys Gly Glu Arg Thr Lys Tyr Ala Asp Cys Ala Lys
1               5                   10                  15

Ser Thr Arg Ala Phe Asp Tyr Leu Ile Tyr Gly Ala Ser Tyr Leu Gln
            20                  25                  30

Ser Cys Gln Gln Thr Arg Phe Ser Pro Asn Thr Phe Gly
         35                  40                  45

<210> SEQ ID NO 44
<211> LENGTH: 48
<212> TYPE: PRT
<213> ORGANISM: Artificial Sequence
<220> FEATURE:
<223> OTHER INFORMATION: C10/1-48 peptide

<400> SEQUENCE: 44

Thr Ile Thr Lys Lys Gly Glu Arg Thr Lys Tyr Ala Asp Cys Ala Lys
1               5                   10                  15

Ser Thr Arg Ala Phe Asp Tyr Trp Leu Ile Tyr Gly Ala Ser Tyr Leu
            20                  25                  30

Gln Ser Cys Gln Gln Thr Arg Phe Ser Pro Asn Thr Phe Gly Gln Gly
         35                  40                  45

<210> SEQ ID NO 45
<211> LENGTH: 46
<212> TYPE: PRT
<213> ORGANISM: Artificial Sequence
<220> FEATURE:
<223> OTHER INFORMATION: H7/1-46 peptide

<400> SEQUENCE: 45

Thr Ile Thr Lys Lys Gly Glu Arg Thr Lys Tyr Cys Ala Lys Ser Thr
1               5                   10                  15

Arg Ala Phe Asp Tyr Trp Leu Ile Tyr Gly Ala Ser Tyr Leu Gln Ser
            20                  25                  30

Cys Gln Gln Thr Arg Phe Ser Pro Asn Thr Phe Gly Gln Gly

```
            35                  40                  45
```

<210> SEQ ID NO 46
<211> LENGTH: 48
<212> TYPE: PRT
<213> ORGANISM: Artificial Sequence
<220> FEATURE:
<223> OTHER INFORMATION: D11/1-48 peptide

<400> SEQUENCE: 46

```
Thr Ile Thr Lys Lys Gly Glu Arg Thr Lys Tyr Ala Asp Cys Ala Lys
1               5                   10                  15

Ser Thr Arg Ala Phe Asp Tyr Trp Leu Ile Tyr Gly Ala Ser Tyr Leu
            20                  25                  30

Gln Ser Cys Gln Gln Thr Arg Phe Ser Pro Asn Thr Phe Gly Gln Gly
        35                  40                  45
```

<210> SEQ ID NO 47
<211> LENGTH: 45
<212> TYPE: PRT
<213> ORGANISM: Artificial Sequence
<220> FEATURE:
<223> OTHER INFORMATION: E1/1-45 peptide

<400> SEQUENCE: 47

```
Thr Ile Thr Lys Lys Gly Glu Arg Thr Lys Tyr Ala Asp Cys Ala Lys
1               5                   10                  15

Ser Thr Arg Ala Phe Asp Tyr Leu Ile Tyr Gly Ala Ser Tyr Leu Gln
            20                  25                  30

Ser Cys Gln Gln Thr Arg Phe Ser Pro Asn Thr Phe Gly
        35                  40                  45
```

<210> SEQ ID NO 48
<211> LENGTH: 43
<212> TYPE: PRT
<213> ORGANISM: Artificial Sequence
<220> FEATURE:
<223> OTHER INFORMATION: C2/1-43 peptide

<400> SEQUENCE: 48

```
Thr Ile Thr Lys Lys Gly Glu Arg Thr Lys Tyr Ala Asp Cys Ala Lys
1               5                   10                  15

Ser Thr Arg Ala Phe Asp Tyr Ile Tyr Gly Ala Ser Tyr Leu Gln Ser
            20                  25                  30

Cys Gln Gln Thr Arg Phe Ser Pro Asn Thr Phe
        35                  40
```

<210> SEQ ID NO 49
<211> LENGTH: 45
<212> TYPE: PRT
<213> ORGANISM: Artificial Sequence
<220> FEATURE:
<223> OTHER INFORMATION: H1/1-45 peptide

<400> SEQUENCE: 49

```
Thr Ile Thr Lys Lys Gly Glu Arg Thr Lys Tyr Ala Asp Cys Ala Lys
1               5                   10                  15

Ser Thr Arg Ala Phe Asp Tyr Leu Ile Tyr Gly Ala Ser Tyr Leu Gln
            20                  25                  30

Ser Cys Gln Gln Thr Arg Phe Ser Pro Asn Thr Phe Gly
        35                  40                  45
```

<210> SEQ ID NO 50
<211> LENGTH: 47
<212> TYPE: PRT
<213> ORGANISM: Artificial Sequence
<220> FEATURE:
<223> OTHER INFORMATION: F5/1-47 peptide

<400> SEQUENCE: 50

Thr Ile Thr Lys Lys Gly Glu Arg Thr Lys Tyr Ala Asp Cys Ala Lys
1               5                   10                  15

Ser Thr Arg Ala Phe Asp Tyr Leu Ile Tyr Gly Ala Ser Tyr Leu Gln
            20                  25                  30

Ser Cys Gln Gln Thr Arg Phe Ser Pro Asn Thr Phe Gly Gln Gly
        35                  40                  45

<210> SEQ ID NO 51
<211> LENGTH: 48
<212> TYPE: PRT
<213> ORGANISM: Artificial Sequence
<220> FEATURE:
<223> OTHER INFORMATION: A10/1-48 peptide

<400> SEQUENCE: 51

Thr Ile Thr Lys Lys Gly Glu Arg Thr Lys Tyr Ala Asp Cys Ala Lys
1               5                   10                  15

Ser Thr Arg Ala Phe Asp Tyr Leu Leu Ile Tyr Gly Ala Ser Tyr Leu
            20                  25                  30

Gln Ser Cys Gln Gln Thr Arg Phe Ser Pro Asn Thr Phe Gly Gln Gly
        35                  40                  45

<210> SEQ ID NO 52
<211> LENGTH: 1218
<212> TYPE: DNA
<213> ORGANISM: Artificial Sequence
<220> FEATURE:
<223> OTHER INFORMATION: scFv-Furin

<400> SEQUENCE: 52

| | |
|---|---|
| atggagctga ggccctggtt gctatgggtg gtagcagcaa caggaacctt ggtcctgcta | 60 |
| gcagctgatg ctcagggcca gaaggtctta ccagtcgcca ccatggtgag cgtggatct | 120 |
| ggtagcggcg gcggcggctc tggtggtggt agatctggtc agccggccat ggccgaggtg | 180 |
| cagctgttgg agtctggggg aggcttggta cagcctgggg ggtccctgag actctcctgt | 240 |
| gcagcctctg gattcacctt tagcagctat gccatgagct gggtccgcca ggctccaggg | 300 |
| aaggggctgg agtgggtctc aacgattacg aagaggggtg agaggacaaa gtacgcagac | 360 |
| tccgtgaagg gccggttcac catctccaga gacaattcca gaacacgct gtatctgcaa | 420 |
| atgaacagcc tgagagccga ggacacggcc gtatattact gtgcgaaaag tactcgtgcg | 480 |
| tttgactact ggggccaggg aaccctggtc accgtctcga gcggtggagg cggttcaggc | 540 |
| ggaggtggca gcggcggtgg cgggtcgacg gacatccaga tgacccagtc tccatcctcc | 600 |
| ctgtctgcat ctgtaggaga cagagtcacc atcacttgcc gggcaagtca gagcattagc | 660 |
| agctatttaa attggtatca gcagaaacca gggaaagccc ctaagctcct gatctatggg | 720 |
| gcatcctatt tgcaaagtgg ggtcccatca aggttcagtg cagtggatc tgggacagat | 780 |
| ttcactctca ccatcagcag tctgcaacct gaagattttg caacttacta ctgtcaacag | 840 |

```
acgcgttttt cgcctaatac gttcggccaa gggaccaagg tggaaatcaa acgggcggcc    900
gcacatcatc atcaccatca cggggccgca gaacaaaaac ccatctcaga agaggatctg    960
aatggggccg caggtgggga tctccaggta gcagtggccg gctgtgtttt cctgctgatc   1020
agcgtcctcc tcctgagtgg gctcacctgg cagcggtgtt caggcttcag cttccgggga   1080
gtgaaagtgt acaccatgga ccgtggcctc atctcctaca aggggctgcc tcctgaggcc   1140
tggcaggagg agtgcccatc tgactcagaa gaggatgagg gccggggtga gaggaccgac   1200
tgtctatttc ttttctag                                                 1218

<210> SEQ ID NO 53
<211> LENGTH: 24
<212> TYPE: DNA
<213> ORGANISM: Artificial Sequence
<220> FEATURE:
<223> OTHER INFORMATION: Nucleic Acid

<400> SEQUENCE: 53
ccctaaccct aaccctaacc ctaa                                            24

<210> SEQ ID NO 54
<211> LENGTH: 28
<212> TYPE: DNA
<213> ORGANISM: Artificial Sequence
<220> FEATURE:
<223> OTHER INFORMATION: Nucleic Acid

<400> SEQUENCE: 54
cccctaaccc ctaaccccta acccctaa                                        28

<210> SEQ ID NO 55
<211> LENGTH: 40
<212> TYPE: DNA
<213> ORGANISM: Artificial Sequence
<220> FEATURE:
<223> OTHER INFORMATION: Nucleic Acid

<400> SEQUENCE: 55
ccccccctaa ccccccctaa ccccccctaa ccccccctaa                           40

<210> SEQ ID NO 56
<211> LENGTH: 26
<212> TYPE: DNA
<213> ORGANISM: Artificial Sequence
<220> FEATURE:
<223> OTHER INFORMATION: Nucleic Acid

<400> SEQUENCE: 56
cccctaaccc taaccccTAA ccctaa                                          26

<210> SEQ ID NO 57
<211> LENGTH: 22
<212> TYPE: DNA
<213> ORGANISM: Artificial Sequence
<220> FEATURE:
<223> OTHER INFORMATION: Nucleic Acid

<400> SEQUENCE: 57
ccccaccctc cccaccctcc cc                                              22

<210> SEQ ID NO 58
<211> LENGTH: 17
<212> TYPE: DNA
```

```
<213> ORGANISM: Artificial Sequence
<220> FEATURE:
<223> OTHER INFORMATION: Nucleic Acid

<400> SEQUENCE: 58
ctatgcggcc ccattca                                                    17
```

NUCLEIC ACID ASSEMBLY, VECTOR, CELL, METHODS AND KIT THEREOF

CROSS-REFERENCE TO RELATED APPLICATIONS

This application is a 371 U.S. National Stage of International Application No. PCT/IB2012/055515, filed Oct. 11, 2012, which claims priority to Indian Patent Application No. 3252/CHE/2011, filed Oct. 12, 2011. The entire disclosures of the above applications are incorporated herein by reference.

TECHNICAL FIELD

The present disclosure relates to a nucleic acid assembly (NAA), comprising sensor domain and handle domain; an assembly interfaceable motif (AIM) and an AIM-nucleic acid assembly complex. It also relates to a vector comprising intracellular targeting motif (ITM) sequence and assembly interfaceable motif sequence and a cell comprising the vector. Further, the instant disclosure also provides a method to obtain the nucleic acid assembly; method of intracellular targeting and kit thereof.

BACKGROUND AND PRIOR ART OF THE DISCLOSURE

Chemical messengers are small, diffusible molecules within living organisms and include second messengers such as ions, hormones, neurotransmitters, cyclic nucleotides etc that play a central role in development and cell function. Methods that are generalized to capture maps of chemical messengers within cells are invaluable in order to understand the manifold functions of second messengers. Methods to obtain chemical maps specific to a given messenger mostly use genetically encodable fluorescent sensors.

In contrast, methods that are generalizable to multiple second messengers tend to use imaging based on CARS, SIMS and MALDI, still need to achieve either adequate temporal resolution or reduce imaging artifacts. Thus obtaining high resolution spatiotemporal chemical maps in living systems using a generalizable methodology is still challenging. A second messenger that plays a crucial role in metabolism, neuronal activity, cell-cycle control and growth is pH. Different second messengers are functionally coupled and act in concert to stringently maintain sub-cellular proton concentrations since pH regulates the activity of key enzymes and ion channels.

Subcellular organelles are bounded by membranes where the intra-organellar pH is stringently regulated. The lumenal pH of various cellular organelles has been mapped primarily using pH-sensitive fluorophore functionalised ligands that bind specifically to receptors that are resident in the relevant organelles. As the receptor shuttles between the plasma membrane and its relevant organelles, the derivatised ligand is ferried by the receptor along its retrograde endocytic pathway. Organelle pH may also be measured by expressing pH sensitive fluorescent proteins fused to peptide sequences that function as organelle localization signals. However these cannot give temporal information on pH changes of a receptor containing compartment while it undergoes maturation.

Thus, most studies have utilized pH reporters in the form of fluorescent pH probes conjugated to endocytosable ligands. However, for the vast majority of cases where (a) the fluorophore conjugation to the ligand either disrupts ligand structure or ligand trafficking and (b) for membrane proteins which have no associated ligands, pH mapping of the relevant compartmental maturation process is still not accessible.

The burgeoning field of DNA nanotechnology has yielded a number of powerful synthetic molecular devices for small molecule sensing in vitro. Yet remarkably, this chemical diversity in sensing has not yet been exploited in cellulo or in vivo. One of the rare examples of DNA-based molecular devices that show quantitative preservation of its sensing functionality both in cellulo and in vivo, is the I-switch. This is a DNA assembly that undergoes a conformational change triggered by acidic pH. Acidic pH causes the formation of a non-Watson-Crick based DNA motif called the I-tetraplex, or i-motif that is then transduced into a large scale conformational change of the overall DNA assembly. The I-switch has therefore been used in living systems as a pH sensor to map spatial and temporal pH changes associated with the maturation of endosomes, by conjugating it with endocytic ligands. However, such DNA devices are not amenable to report on the chemical environments of the vast majority of proteins.

DNA has been used to build nanomechanical devices with potential in cellulo and in vivo applications. However, their in cellulo applications in different biological pathways are limited due to current device response times as well as limitations associated with their delivery to precise intracellular locations.

STATEMENT OF THE DISCLOSURE

Accordingly, the present disclosure relates to a nucleic acid assembly (NAA) comprising sensor domain and handle domain, optionally along with sensor molecule, wherein the nucleic acid assembly is selected from group comprising SEQ ID Nos. 1 to 21 or any combinations thereof; an assembly interfaceable motif (AIM) comprising intracellular targeting motif (ITM) conjugated with an artificial receptor, wherein the artificial receptor is selected from group comprising single chain variable fragment (scFv), transcription factor, Zn-fingered protein, leucine zipper, DNA binding immunoglobulin, DNA binding protein or any combinations thereof; an assembly interfaceable motif (AIM)-nucleic acid assembly (NAA) complex, wherein the nucleic acid assembly as mentioned above is conjugated with the assembly interfaceable motif (AIM) as mentioned above through the artificial receptor; a vector comprising assembly interfaceable motif (AIM) mentioned above, optionally along with intracellular targeting motif (ITM); a cell comprising vector expressing assembly interfaceable motif (AIM) as mentioned above, optionally along with intracellular targeting motif (ITM); a method of arriving at a cell comprising a vector as mentioned above, said method comprising acts of—a) obtaining a vector comprising assembly interfaceable motif (AIM) optionally along with intracellular targeting motif (ITM), and b) transfecting a cell with the vector to express the assembly interfaceable motif (AIM) optionally along with the intracellular targeting motif (ITM) to obtain the cell; a method for obtaining nucleic acid assembly comprising sensor domain and handle domain, optionally along with sensor molecule, wherein the nucleic acid assembly is selected from group comprising SEQ ID Nos. 1 to 21 or any combinations thereof, said method comprising acts of—a) designing complementary strands coding for sensor domain and handle domain, b) positioning and annealing of the complementary strands in solution to obtain the nucleic acid assembly, and c) optionally adding the sensor molecule to the Nucleic acid assembly; a method of obtaining nucleic acid assembly [NAA]-assembly interfaceable motif [AIM] complex as mentioned above, said method comprising acts of—a) obtaining nucleic acid assembly by method as mentioned above, b) obtaining a vector comprising assembly interfaceable motif (AIM), c) transfecting a cell with the vector to express the assembly interfaceable motif (AIM) and obtain the AIM on the transfected cell, and d) incubating the nucleic acid assembly with the cell comprising the AIM to obtain the nucleic acid assembly [NAA]-assembly interfaceable motif [AIM]complex; a method of intracellular targeting of Nucleic acid assembly-Assembly interfaceable motif (AIM-NAA) complex as mentioned above, said method comprising acts of—a) obtaining nucleic acid assembly by method as mentioned above, b) obtaining a vector comprising assembly interfaceable motif (AIM), c) transfecting a cell with the vector to express the assembly interfaceable motif (AIM) and obtain the AIM on the transfected cell, d) incubating the nucleic acid assembly with the cell comprising the AIM for obtaining the nucleic acid assembly [NAA]-assembly interfaceable motif [AIM] complex on the cell, and e) re-incubating the complex for cellular uptake and intracellular targeting of the Nucleic acid assembly-Assembly interfaceable motif (AIM-NAA) complex; a kit for obtaining nucleic acid assembly [NAA]-assembly interfaceable motif [AIM] complex, said kit comprising components selected from group comprising nucleic acid assembly as mentioned above, AIM as mentioned above, vector as mentioned above, cell as mentioned above and instruction manual or any combinations thereof; a method of assembling a kit as mentioned above, said method comprising act of combining components selected from group comprising nucleic acid assembly as mentioned above, AIM as mentioned above, vector as mentioned above, cell as mentioned above and instruction manual or any combinations thereof; a kit for intracellular targeting of nucleic acid assembly [NAA]-assembly interfaceable motif [AIM] complex, said kit comprising components selected from group comprising nucleic acid assembly as mentioned above, AIM as mentioned above, nucleic acid assembly [NAA]-assembly interfaceable motif [AIM] complex as mentioned above, vector as mentioned above, cell as mentioned above and instruction manual or any combinations thereof; and a method of assembling a kit as mentioned above, said method comprising act of combining components selected from group comprising nucleic acid assembly as mentioned above, AIM as mentioned above, nucleic acid assembly [NAA]-assembly interfaceable motif [AIM] complex as mentioned above, vector as mentioned above, cell as mentioned above and instruction manual or any combinations thereof.

BRIEF DESCRIPTION OF THE ACCOMPANYING FIGURES

The patent or application file contains at least one drawing executed in color. Copies of this patent or patent application publication with color drawing(s) will be provided by the Patent and Trademark Office upon request and payment of the necessary fee.

In order that the disclosure may be readily understood and put into practical effect, reference is made to exemplary embodiments as illustrated with reference to the accompanying figures. The figures together with a detailed description below, are incorporated in and form part of the specification, and serve to further illustrate the embodiments and explain various principles and advantages, in accordance with the present disclosure where:

FIG. 1 Depicts the working principle of the DNA pH sensor/Nucleic Acid Assembly. (a) Schematic description of ligand free delivery method using NAA and AIM. At neutral/basic pH, it exists as a mismatched duplex and at acidic pH, the functional C-rich domain forms an intramolecular i-motif (green strand). Donor (gray circle) and acceptor (black circle) fluorophores are used as reporters of the conformational change. The gray region on the pH sensor represents a dummy duplex 'handle' domain to which a recombinant antibody that is a part of AIM (scFv, gray helices) binds specifically. (b) Fusion of this scFv domain onto the lumenal portion of a membrane protein such as Furin (Also part of AIM, brown) results in recognition of the DNA assembly from extracellular milieu and specific transport into a defined intracellular organelle. (c) Donor (D) to acceptor (A) ratio measurements on dually labeled Nucleic Acid Assemblies as a function of pH. Ratio of fluorescence intensities at 520 nm and 669 nm when excited at 488 nm of the respective Nucleic acid assembly in clamping buffer at the indicated pH is shown a function of pH. (d) Folding times of Nucleic Acid Assembly sensors as a function of pH. (e) Schematic representation of the immobilized DNA strands used in scFv binding specificity studies. (f) Binding efficiency of selected scFv (clone C1) to various DNA epitopes: ssDNA, dsDNA, $R_1$, $R_2$ and $R_M$. (g) Binding efficiency of scFv to immobilized dsDNA in the presence of increasing amounts of competitor dsDNA. In all cases, absorbance at 450 nm is normalized with respect to binding in the absence of competitor DNA. All experiments are performed in triplicate and expressed as mean±SD.

FIG. 2 shows pH sensing domain of four representative Nucleic Acid Assembly sensors showing paired regions (black lines) and engineered mismatches shown in red.

FIG. 3 shows the characterization of the Nucleic Acid Assembly sensors using Circular Dichroism (CD) spectroscopy. (a) CD spectra of the Nucleic Acid Assembly, $I^4$, at pH 8.3 (black), pH 4 (dark gray) and difference spectra (pH 4-pH 8.3, light gray). (b) CD signal at 292 nm of different Nucleic Acid assemblies as a function of pH. Mean CD intensity is plotted against pH after normalizing individual traces.

FIG. 4 shows steady state fluorescence measurements on Nucleic Acid Assembly.

FIG. 5 shows screening of dsDNA binding scFvs. (a) Sequence of the dsDNA epitope used for phage display screening. 5'-Biotin modification is used to immobilize the 35 bp dsDNA epitope to Streptavidin conjugated magnetic beads. Fonts in light gray represent region 1 ($R_1$), fonts in dark gray represent region 2 ($R_2$) and fonts in underlined italics represent the region $R_M$. (b) Schematic representation of dsDNA epitope used for screening. (c) Yield of phage after each round of selection is shown by counting colonies present in different dilutions of eluted phage particle after triethyl amine treatment.

FIG. 6 shows screening of DNA sequence-specific scFvs. (a) Schematic representation of DNA strands used in sequence specific ELISA screens—$R_1$ (red font), $R_2$ (green font) and $R_M$ (blue font). (b (i-iii)) ELISA results obtained after incubating protein supernatant of indicated clones with epitopes shown in (a): (i) Region $R_1$, (ii) $R_2$, (iii) $R_M$. Arrowheads are indicative of positive clones specific for respective regions. (c-e) Quantification of the binding efficiencies of some selected scFvs to various DNA epitopes. Experiments are performed in triplicate and are presented as mean±SD.

FIG. 7 shows sequence alignment of dsDNA binding scFvs. CDRs of 21 scFvs are aligned in ClustalW2—Multiple Sequences Alignment tool and represented as color coded in boxes for conserved residues. Red arrowhead: $R_1$ specific clones, Green arrowhead: $R_2$ specific clones. Numbers represent percentage conserved residues at indicated positions along the sequences of the clone.

FIG. 8 shows scFv production and purification.

FIG. 9 shows determination of binding constant using scFv C1 with 35 bp dsDNA. (a) Biotinylated 35 bp dsDNA is immobilized at different concentrations with a constant scFv amount (300 pmoles). (b) Various concentrations of scFv are added to the wells containing dsDNA (25 pmoles) immobilized at the same concentration. After dsDNA-scFv incubation, binding is measured using ELISA and absorbance at 450 nm is normalized with respect to the highest observed intensity and plotted as a function of concentration. The lines are intended only for visual clarity.

FIG. 10 shows characterization of scFv-Furin chimera expression and localization in cellulo. (a) Western blot analysis of scFv-Furin post transfection in HeLa cells probed using anti His-Tag antibody. Lane 1: scFv-Furin, 2: Marker (Bio rad), 3: scFv Furin (lower concentration), 4: Marker (NEB), 5: GFP transfected HeLa cells 6: Untransfected HeLa cells. (b) scFv-Furin transfected and (c) untransfected HeLa cells are fixed and treated with mouse anti His-tag and Myc-tag antibodies and then probed with Flourescein conjugated goat-anti mouse secondary antibody. (d) scFv-Furin transfected HeLa cells treated with mouse anti His-Tag and rabbit anti TGN46 antibody to mark scFv-Furin and TGN46 respectively and then probed with the relevant secondary antibodies. Scale bar: 10 µm.

FIG. 11 shows scFv domain of scFv-Furin functions as an artificial receptor for Nucleic acid assembly. scFv-Furin expressing (a) HeLa cells and (b) TRVb-1 cells labeled with 500 nM $I^4_{A488/A647}$ for 1 hour at 37° C., washed, chased for 3 hours and then imaged. (c & d) Quantification of images represented in (a-b). Mean intensity at 520 nm of 20 cells±SEM is shown. Af=Autofluorescence, Un=Untransfected, scFv=scFv-Furin expressing cells. (e) Schematic representation of competitive uptake of Nucleic Acid Assembly by scFv-Furin expressing HeLa cells. $I^4_{A488/A647}$ uptake (1): in the presence of no added competitor, (2): in the presence of 25 µM of a dsDNA sequence that lacks $d(AT)_4$ tag, (3): in the presence of 25 µM of $I^4$ dsDNA. (f) Mean fluorescence intensity at 647 nm normalized with respect to (1) and presented as percentage intensity of internalized $I^4_{A488/A647}$. All the experiments are performed in triplicate. Scale Bar: 10 µm.

FIG. 12 shows trafficking of Nucleic Acid Assembly. (a) Time dependent accumulation of Nucleic Acid Assembly near perinuclear regions. scFv expressing HeLa cells are labeled with $I^4_{A488/A647}$ for 10 min at 37° C. and chased for 0 min, 30 min and 120 min in complete medium at 37° C. (b) scFv-Furin and GFP Furin are co-transfected and co-pulsed with $I^4_{A647}$ (I-647) and Alexa 594 conjugated anti-GFP antibody (A-594 anti-GFP). After a 3 hour chase, cells are fixed with 4% PFA for 15-20 min and imaged. (d) scFv-Furin expressing TRVb-1 cells are pulsed with TMR-Dextran (TMR Dex) and $I^4_{A488/A647}$ (I-647) at 37° C. for 1.5 hours, chased for 3 hours and then imaged. (c, e) Quantification of co-localization between $I^4_{A488/A647}$ and endosomal markers used in (b-d). Experiments are performed in duplicate. Error Bar: Mean of 11 cells±SD. Scale Bar: 5 µm.

FIG. 13 shows retrograde transport of Nucleic acid assembly by scFv-Furin. (a) scFv-Furin expressing HeLa cells pulsed with $I^4_{A488/A647}$ and Transferrin-A568 (Tfn$_{568}$) for 10 min at 37° C., washed and imaged immediately. (b) scFv-Furin expressing HeLa cells labeled as described in (a), chased for 2 hours and imaged. (c) scFv-Furin expressing HeLa cells are pulsed with TMR-Dextran and $I^4_{A488/A647}$ at 37° C. for 1.5 hours, chased for 3 hours and then imaged. (d-f) Quantification of co-localization between $I^4_{A488/A647}$ and endosomal markers used in (a-c). Error Bar: Mean of 11 cells±SD. Experiments are performed in duplicate. Scale Bar: 5 µm.

FIG. 14 shows in cellulo performance of $I^4_{A488/A647}$. Representative pseudocolour D/A map of HeLa cells clamped at indicated pH values is shown along with their respective fluorescence images (in 520 channel) shown in grayscale.

FIG. 15 shows in cellulo performance of Nucleic acid assembly. (a-f) scFv-Furin expressing HeLa cells labeled with $I^3_{A488/A647}$ for 1.5 hours at 37° C. and clamped at indicated pH values using pH clamping buffer. (a-f) Representative pseudocolour D/A map of HeLa cells clamped at indicated pH values. (g) Fold change in D/A values of two different Nucleic acid assemblies ($I^3_{A488/A647}$ and $I^4_{A488/A647}$) in vitro (light gray) and in cellulo (dark gray) computed from the D/A values at pH 7.0 and pH 5.0 (h) Intracellular calibration curve of $I^4_{A488/A647}$ showing D/A intensity ratios of 120 endosomes as a function of pH (gray). Also shown is the in vitro pH response curve of the same in pH clamping buffer (black). Insets: Magnification of region of interest. Error Bar: Mean of experiments in duplicate. Scale Bar: 10 µm.

FIG. 16 shows spatiotemporal pH maps of retrogradely trafficked scFv-Furin. scFv-Furin expressing HeLa cells are labeled with $I^4_{A488/A647}$ for 10 min at 37° C. and (a-b) immediately imaged. (c-d) cells are chased for 30 min and then imaged. (e-f) Cells are chased for 2 hours and then imaged. (g-h) scFv-Furin expressing HeLa cells are labeled with $I^4_{A488/A647}$ for 2 hours, washed and then imaged. (i-l) Population of histogram of endosomes as a function of their D/A ratios. (i-k) n=250 endosomes, (l), n=330 endosomes. Insets: Magnification of region of interest. Scale bar: 10 µm.

Figures 20, 20A:
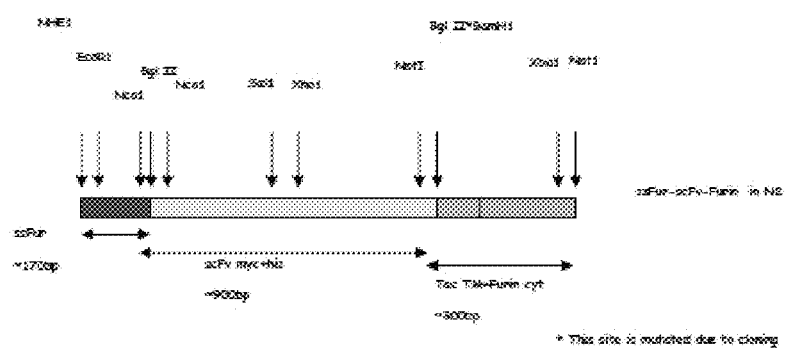

FIG. 20 (a) provides the complete sequence of scFv-Furin along with restriction enzyme cut sites. FIG. 20 (b) depicts the sequence of scFv-Furin complex.

Figure 21:
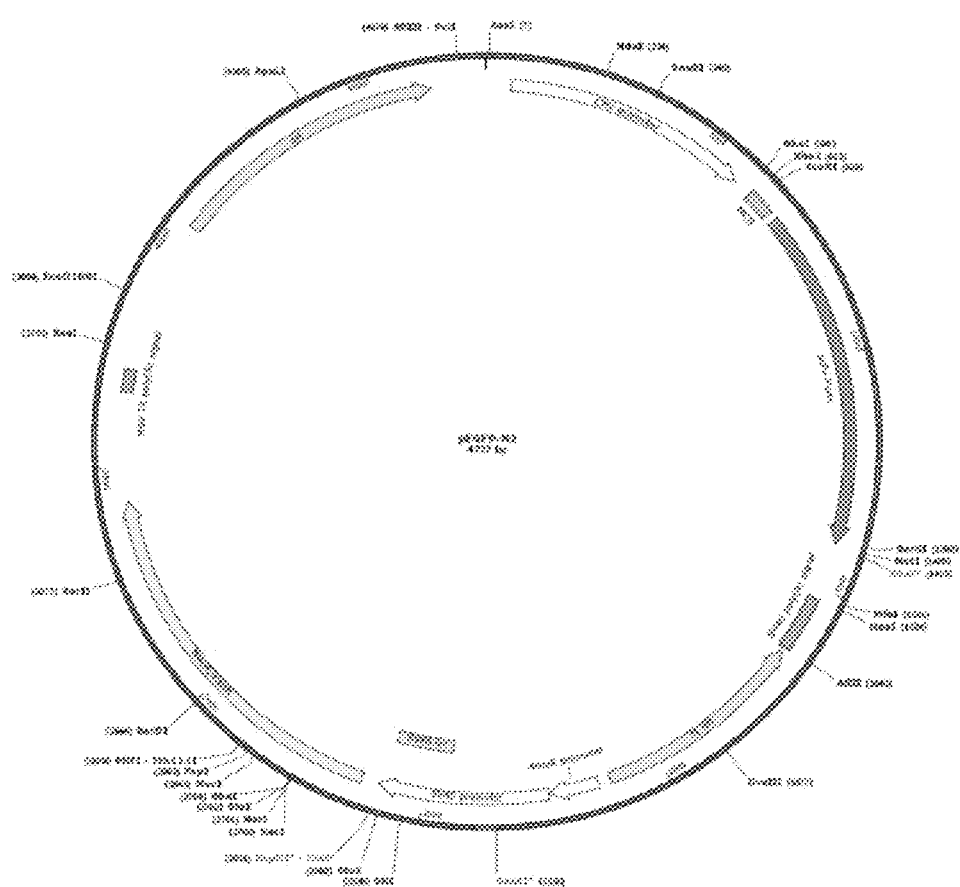

FIG. 21 depicts the EGFP-N2 vector with scFv-Furin sequence.

DETAILED DESCRIPTION OF THE DISCLOSURE

The present disclosure relates to a nucleic acid assembly (NAA) comprising sensor domain and handle domain, optionally along with sensor molecule; wherein the nucleic acid assembly is selected from group comprising SEQ ID Nos. 1 to 21 or any combinations thereof.

The present disclosure also relates to an assembly interfaceable motif (AIM) comprising intracellular targeting motif (ITM) conjugated with an artificial receptor; wherein the artificial receptor is selected from group comprising single chain variable fragment (scFv), transcription factor, Zn-fingered protein, leucine zipper, DNA binding immunoglobulin, DNA binding protein or any combinations thereof.

The present disclosure also relates to an assembly interfaceable motif (AIM)-nucleic acid assembly (NAA) complex, wherein the nucleic acid assembly as mentioned above is conjugated with the assembly interfaceable motif (AIM) as mentioned above through the artificial receptor.

The present disclosure also relates to a vector comprising assembly interfaceable motif (AIM) as mentioned above, optionally along with intracellular targeting motif (ITM).

The present disclosure also relates to a cell comprising vector expressing assembly interfaceable motif (AIM) as mentioned above, optionally along with intracellular targeting motif (ITM).

The present disclosure also relates to a method of arriving at a cell comprising a vector as mentioned above, said method comprising acts of:
a) Obtaining a vector comprising assembly interfaceable motif (AIM) optionally along with intracellular targeting motif (ITM); and
b) transfecting a cell with the vector to express the assembly interfaceable motif (AIM) optionally along with the intracellular targeting motif (ITM) to obtain the cell.

The present disclosure also relates to a method for obtaining nucleic acid assembly comprising sensor domain and handle domain, optionally along with sensor molecule, wherein the nucleic acid assembly is selected from group comprising SEQ ID Nos. 1 to 21 or any combinations thereof, said method comprising acts of:
a) designing complementary strands coding for sensor domain and handle domain;
b) positioning and annealing of the complementary strands in solution to obtain the nucleic acid assembly; and
c) optionally adding the sensor molecule to the Nucleic acid assembly.

The present disclosure also relates to a method of obtaining nucleic acid assembly [NAA]-assembly interfaceable motif [AIM] complex as mentioned above, said method comprising acts of:
a) obtaining nucleic acid assembly by method as mentioned above;
b) obtaining a vector comprising assembly interfaceable motif (AIM);
c) transfecting a cell with the vector to express the assembly interfaceable motif (AIM) and obtain the AIM on the transfected cell; and
d) incubating the nucleic acid assembly with the cell comprising the AIM to obtain the nucleic acid assembly [NAA]-assembly interfaceable motif [AIM] complex.

The present disclosure also relates to a method of intracellular targeting of Nucleic acid assembly-Assembly interfaceable motif (AIM-NAA) complex as mentioned above, said method comprising acts of:
a) obtaining nucleic acid assembly by method as mentioned above;
b) obtaining a vector comprising assembly interfaceable motif (AIM);
c) transfecting a cell with the vector to express the assembly interfaceable motif (AIM) and obtain the AIM on the transfected cell;
d) incubating the nucleic acid assembly with the cell comprising the AIM for obtaining the nucleic acid assembly [NAA]-assembly interfaceable motif [AIM] complex on the cell; and
e) re-incubating the complex for cellular uptake and intracellular targeting of the Nucleic acid assembly-Assembly interfaceable motif (AIM-NAA) complex.

In an embodiment of the present disclosure, the sensor molecule of the NAA is selected from group comprising physiological sensor, small molecule sensor, organic molecules, proteins, nucleic acids, metabolites, drugs and their derivatives, amino acids, nucleotides and its derivatives, biological cofactors, antibiotics, vitamins, proteins, small peptides, toxins, lipids, growth factors, hormones and enzymes or any combinations thereof.

In another embodiment of the present disclosure, the AIM is selected from group comprising nucleic acid binding protein, recombinant antibody, transcription factor, Zn-finger protein, leucine zipper, peptide, proteins that posses natural receptor, trafficking protein, toxins, virus, viral coat protein, cell penetrating peptide, signal sequence, intracellular targeting sequence, small organic molecule, endocytic ligand, enzyme, aptamer against trafficking protein or any combinations thereof.

In yet another embodiment of the present disclosure, the ITM is selected from group comprising endocytosable plasma membrane protein, protein that possesses a natural receptor, trafficking protein, toxins, virus, viral coat protein, cell penetrating peptide, signal sequence, intracellular targeting sequence, small organic molecule and endocytic ligand or any combinations thereof; and the artificial receptor is selected from group comprising single chain variable fragment (scFv), transcription factor, Zn-fingered protein, leucine zipper, DNA binding immunoglobulin, DNA binding protein or any combinations thereof.

In still another embodiment of the present disclosure, the ITM is Furin and binds to nucleic acid assembly (NAA) by way of hydrogen bonding interactions.

In still another embodiment of the present disclosure, the vector is selected from group comprising plasmids, viruses, or viral vectors, cosmids, phagemids and artificial chromosomes.

In still another embodiment of the present disclosure, the cell is eukaryotic cell and is selected from group comprising HeLa cell, TRV-1 and IA2.2 cell.

In still another embodiment of the present disclosure, the incubating is carried out at temperature ranging from about 4° C. to about 37° C.

In still another embodiment of the present disclosure, the re-incubating is carried out at temperature ranging from about 20° C. to about 37° C.; and the intracellular targeting is to endosome.

The present disclosure also relates to a kit for obtaining nucleic acid assembly [NAA]-assembly interfaceable motif [AIM] complex, said kit comprising components selected from group comprising nucleic acid assembly as mentioned above, AIM as mentioned above, vector as mentioned above, cell as mentioned above and instruction manual or any combinations thereof.

The present disclosure also relates to a method of assembling a kit as mentioned above, said method comprising act of combining components selected from group comprising nucleic acid assembly as mentioned above, AIM as mentioned above, vector as mentioned above, cell as mentioned above and instruction manual or any combinations thereof.

The present disclosure also relates to a kit for intracellular targeting of nucleic acid assembly [NAA]-assembly interfaceable motif [AIM] complex, said kit comprising components selected from group comprising nucleic acid assembly as mentioned above, AIM as mentioned above, nucleic acid assembly [NAA]-assembly interfaceable motif [AIM] complex as mentioned above, vector as mentioned above, cell as mentioned above and instruction manual or any combinations thereof.

The present disclosure also relates to a method of assembling a kit as mentioned above, said method comprising act of combining components selected from group comprising nucleic acid assembly as mentioned above, AIM as mentioned above, nucleic acid assembly [NAA]-assembly interfaceable motif [AIM] complex as mentioned above, vector as mentioned above, cell as mentioned above and instruction manual or any combinations thereof.

In another embodiment of the present disclosure, the signal sequence is localization signal sequence selected from a group comprising organellar localization signal sequence and cytoplasmic localization signal sequence. A localization signal sequence is a peptide sequence that allows a protein to localize at desired organelles or cell surface.

The present disclosure uses signal sequence of Furin. This sequence allows targeting of scFv-Furin into the endoplasmic reticulum for folding, followed by delivery to Golgi complex from where it directed to plasma membrane for expression.

The present disclosure relates to a molecule which is a nucleic acid assembly (NAA) comprising a sensor domain and handle domain. A targeting strategy enabled by an assembly interfaceable motif (AIM) attachable to any portion of the NAA is described in FIGS. 1*a* and 1*b*. AIM is interfaced with locations on NAA that are similar but not restricted to a tag sequence located within the handle domain. AIM is interfaced to NAA using two modes (i) covalent attachment and (ii) non covalent recognition. NAA and AIM are classified as any functional NAA including but not limited to DNA polyhedra, DNA sensors, RNA nanostructures, DNA plasmids being illustrative examples.

In an embodiment of the present disclosure, the Intracellular Targeting Motif (ITM), either alone, or as part of the AIM, attaches covalently and directly to the NAA. In other words, ITM can bind by itself to the NAA through hydrogen bonding or it can bind through the AIM which comprises of the ITM [for ex.: Furin] and the Artificial receptor [for ex.: antibody such as scFv].

FIG. 1*b* presents a schematic description of ligand free delivery method, wherein a Nucleic Acid Assembly (NAA) is recognized and delivered inside living cells by Assembly Interfaceable Motif (AIM) containing an Intracellular Targeting Motif (ITM).

In an embodiment of the present disclosure, the ITM or the intracellular targeting motif consists of Cytoplasmic domain of Furin.

In another embodiment of the present disclosure, the NAA is similar but not restricted to assemblies made from natural nucleobases, natural modified bases (such as 6-keto purine, xanthine, 5-methylcytosine or 2-aminopurine) or unnatural modified bases (such as thioguanine or 8-oxoguanine, deazapurine or azapurine), or analogs of bases such as universal bases (such as nebularin, nitroindole or nitropyrrole derivatives), synthetic derivatives of nucleobases (such as but not restricted to bromo, fluoro substituted), nucleic acid analogs similar but not restricted to PNA, LNA, morpholino, methyl phosphonate, phosphorothipate, 2'-O-modified oligos etc.

In an embodiment of the present disclosure, the sensor molecule is selected from group comprising physiological sensor, small molecule sensor, organic molecules, proteins, nucleic acids, metabolites, drugs and their derivatives, amino acids, nucleotides and its derivatives, biological cofactors, antibiotics, vitamins, proteins, small peptides, toxins, lipids, growth factors, hormones and enzymes. Further, the handle domain comprises of nucleotide sequences.

In another embodiment of the present disclosure, the AIM is selected from group comprising nucleic acid-binding proteins similar to but not restricted to nucleic acid binding antibodies, recombinant antibodies, recombinant antibodies conjugated to a signal sequence, transcription factors, Zn-finger proteins, leucine zippers and peptides. AIM is extended to any molecules similar to but not restricted to proteins that posses a natural receptor, a protein that traffics between intracellular locations via the plasma membrane, toxins, viruses and viral coat proteins, cell penetrating peptides, signal sequences, intracellular targeting sequences, small organic molecules, endocytic ligands, enzymes and aptamers against a trafficking protein.

In a preferred embodiment of the present disclosure, the AIM comprises Furin conjugated to scFv.

The ITM is selected from a group comprising a protein similar to but not restricted to any plasma membrane protein that is endocytosable, any proteins that posses a natural receptor, a protein that traffics between intracellular locations via the plasma membrane, toxins, viruses and viral coat proteins, cell penetrating peptides, signal sequences, intracellular targeting sequences, small organic molecules, endocytic ligands and trafficking proteins.

In an embodiment of the present disclosure, the vector comprises signal sequence, assembly interfaceable motif (AIM), intracellular targeting motif (ITM) and the vector is optimized for the host cell. The cell is selected from group comprising any eukaryotic cells in culture or primary cells, most precisely plant cells, mammalian cells, fly cells and yeast cells.

In the present disclosure, a NAA [Nucleic Acid Assembly] or a molecular design of DNA pH sensor with response times that are nearly 20 fold faster is presented. Further, by changing the sequence of the pH sensitive domain of the DNA sensor, tuning of their pH sensitive regimes and creation of a family of DNA sensors spanning pH ranges from pH about 4.0 to about 7.6 is also conducted. This sensor design of the NAA also incorporates a 'handle' domain. A recombinant antibody is engineered (example: scFv) that binds sequence specifically to the handle domain and acts as an artificial receptor for the whole family of DNA pH sensors or the NAAs. When the scFv is fused to a membrane protein or the ITM (example: Furin) that traffics via the cell surface, the scFv conjugated Furin or the AIM binds to the 'handle' domain of the NAA and ferries the DNA pH sensor or the NAA along the Furin endocytic pathway. Alternatively, the membrane protein or the ITM (example: Furin) can bind individually to the handle domain of the NAA as well.

After endocytosis, the DNA nanodevice or the AIM-NAA conjugate retains its functionality in cellulo and provides spatiotemporal pH maps of retrogradely trafficking the Furin or the ITM inside living cells. This molecular technology is useful to specifically localize DNA nanoarchitectures within different organelles of a living cell. Further, scFv conjugated protein or AIMs are used to site-specifically attach diverse proteins to DNA nanostructures for bioanalytical applications selected from group comprising DNA & RNA aptamer delivery for sensing small molecule dynamics, drug delivery using DNA cages, delivery of antisense oligonucleotides for therapeutics and delivery of plasmid DNA for analysis of gene expressions.

The advantage of a rationally designed DNA-based scaffold that functions as a chemical switch or sensor is its ready amenability to design changes without compromising on the functionality. Further, by changing the sequences of the chemically responsive domain, one tunes sensor affinity to the analyte and thus to response regimes of the sensor.

In the present disclosure, a molecular design is outlined, with at least 20 fold faster response times when compared with the conventional I-switch.

Further, the instant disclosure also elaborates on the engineering of an artificial DNA binding protein [example scFv] that binds specifically to the 'handle' domain of the sensor that is fused to the intracellular protein of choice [example Furin] This enables pH mapping of compartment maturation of the desired protein in a ligand-free manner and thus positions DNA-based sensors to investigate a significantly larger number of currently inaccessible protein environments. The present disclosure also demonstrates proof of concept by pH mapping in different cell types by the protein Furin, whose trafficking is well-studied and yet whose pH maps have remained inaccessible thus far.

In an embodiment of the instant disclosure, the sensor domain of the Nucleic Acid Assembly consists of oligonucleotides described in Table 1 and annealing of the oligonucleotides will provide different sensors. The handle domain is inbuilt in sensor domain so annealing will provide a scaffold which consists of sensor domain and handle domain and is called Nucleic Acid Assembly. When NAA is pulsed or incubated with cells expressing scFv-Furin, scFv recognizes NAA and the whole complex can be called AIM-NAA complex. Further scFv-conjugated to furin is Assembly Interfaceable Motif (AIM) and can be expressed by transfecting the vector described in FIG. 19. In the same plasmid, only the cytoplasmic domain of furin is called Intracellular Targeting Motif (ITM).

The present disclosure is further elaborated with the help of following examples and associated figures. However, these examples should not be construed to limit the scope of the present disclosure.

EXAMPLES

Example 1

Tuning the pH Sensitive Regime of a NAA

TABLE 1

Oligonucleotides comprising Nucleic acid assembly Sequences used and associated nomenclature of samples in the present study. Nucleic acid assemblies incorporating a pH responsive segment Cn-Cn-Cn-Cn are referred to as $I^n$ when they carry no fluorescent labels. Thus, $I^3$ is formed from a 1:1 mixture of $I^3$ and $I^{3'}$, $I^4$ from a 1:1 mixture of $I^4$ and $I^{4'}$, $I^7$ from a 1:1 mixture of $I^7$ and $I^{4'}$, $I^{3-4}$ from a 1:1 mixture of $I^{3-4}$ and $I^{4'}$, $I^{c-myc}$ from a 1:1 mixture of $I^{c-myc}$ and $I^{c-myc'}$.

| Name | SEQ ID Nos | Sequence |
|---|---|---|
| $I^4$ | 1 | 5'-cccctaacccctaaccccctaaccccatatatatcctagaacgacagacaaacagtgagtc-3' |
| $I^7$ | 2 | 5'-ccccccctaacccccccctaaccccccctaacccccccatatatcctagaacgacagacaaacagtgagtc-3' |
| $I^{C3-C4}$ | 3 | 5'-cccctaaccctaaccctaacccatatatatcctagaacgacagacaaacagtgagtc-3' |
| $I^{4'}$ | 4 | 5'-gactcactgtttgtctgtcgttctaggatatatattttgttatgtgttatgtgttat-3' |
| $I^3$ | 5 | 5'-ccctaaccctaaccctaacccatatatatcctagaacgacagacaaacagtgagtccgcattgttacat-3' |
| $I^{3'}$ | 6 | 5'-atgtaacaatgcggactcactgtttgtctgtcgttctaggatatatatttgttagtgttagtgttat-3' |
| $I^{C-myc}$ | 7 | 5'-ccccaccctccccaccctccccatatatatcctagaacgacagacaaacagtgagtc-3' |
| $I^{C-myc'}$ | 8 | 5'-gactcactgtttgtctgtcgttctaggatatatattttgtgagtgtgtgtag-3' |
| $I^4_{A488}$ | 9 | 5'-Alexa488-cccctaaccctaaccctaaccccatatatcctagaacgacagacaaacagtgagtc-3' |
| $I^3_{A488}$ | 10 | 5'-Alexa488-ccctaaccctaaccctaacccatatatatctagaacgacagacaaacagtgagtc-3' |
| $I^7_{A488}$ | 11 | 5'-Alexa488-ccccccctaacccccccctaaccccccctaaccccccatatatatcctagaacgacagacaaacagtgagtc-3' |
| $I^4_{A647}$ | 12 | 5'-gactcactgtttgtctgtcgttctaggatatatattttgttatgtgttatgtgttat-3'-Alexa647 |
| ssDNA | 13 | 5'-Biotin-aaaagactcactgtttgtctgtcgttctaggatatatat-3' |
| ssDNA' | 14 | 5'-atatatatcctagaacgacagacaaacagtgagtc-3' |
| Region 1 | 15 | 5'-atatatatcctag-3' |
| Region 2 | 16 | 51-cgacagacaaaca-3' |

TABLE 1-continued

Oligonucleotides comprising Nucleic acid assembly
Sequences used and associated nomenclature of samples in
thepresent study. Nucleic acid assemblies incorporating
a pH responsive segment Cn-Cn-Cn-Cn are referred
to as $I^n$ when they carry no fluorescent labels.
from a 1:1 mixture of $I^3$ and $I^{3'}$, $I^4$ from a 1:1 mixture
Thus, $I^3$ is formed of $I^4$ and $I^{4'}$, $I^7$ from a 1:1 mixture
of $I^7$ and $I^{4'}$, $I^{3-4}$ from a 1:1 mixture of $I^{3-4}$ and $I^{4'}$,
$I^{c-myc}$ from a 1:1 mixture of $I^{c-myc}$ and $I^{c-myc'}$.

| Name | SEQ ID Nos | Sequence |
|---|---|---|
| Region M | 17 | 5'-cctagaacgacag-3' |
| $I^{comp}$ | 18 | 5'-atatatatcctagaacgacagacaaacagtgagtccgcat tgttacat-3' |
| $I^{comp'}$ | 19 | 5'-atgtaacaatgcggactcactgtttgtctgtcgttctagg atatatat-3' |
| $I^{non\ comp}$ | 20 | 5'-aggctttaaataccggcatg-3' |
| $I^{non\ comp'}$ | 21 | 5'-catgccggtatttaaagcct-3' |
| pHENseq | 22 | 5'-ctatgcggccccattca-3' |

Fluorescently labeled Nucleic Acid assemblies indicate the respective fluorophore in the subscript, where e.g., $I^3_{A488/A647}$ is formed from $I^3_{A488}$ and $I^{3'}_{A647}$, $I^4_{A488/A647}$ from $I^4_{A488}$ and $I^{4'}_{A647}$, $I^4_{A488}$ from $I^4_{A488}$ and $I^{4'}$. The 35 bp dsDNA epitope is formed from ssDNA and ssDNA', $R_1$: ssDNA and Region 1, $R_2$: ssDNA and Region 2, $R_M$: ssDNA and Region M. $I^{comp}$: $I^{comp}$ and $I^{comp'}$ and $I^{non\ comp}$: $I^{non\ comp}$ and $I^{non\ comp'}$.

In an embodiment of the present disclosure, the sequences that are used as Nucleic acid assemblies are represented by SEQ ID Nos. 1-21.

Figure 1:
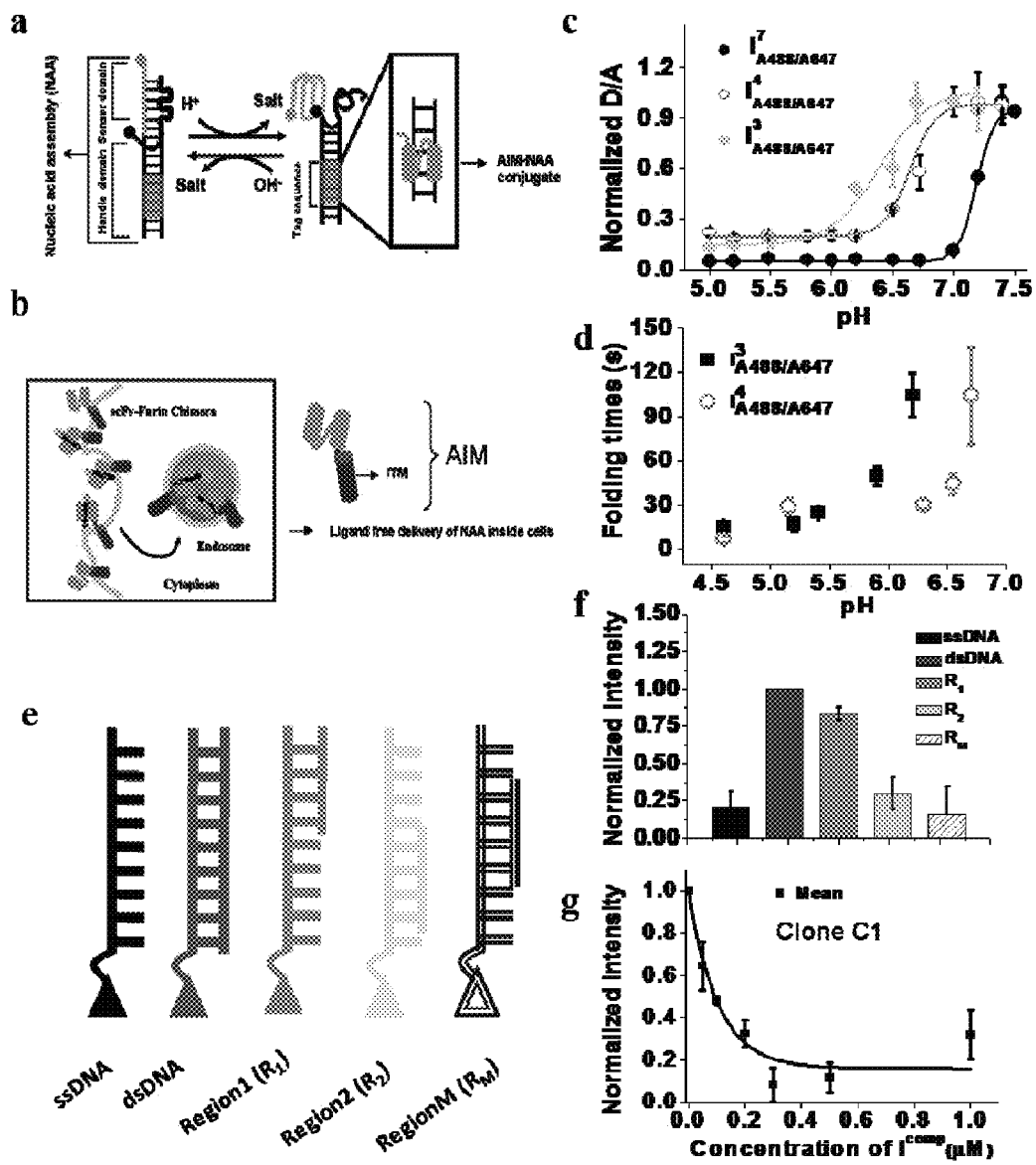
Figures 2, 3:
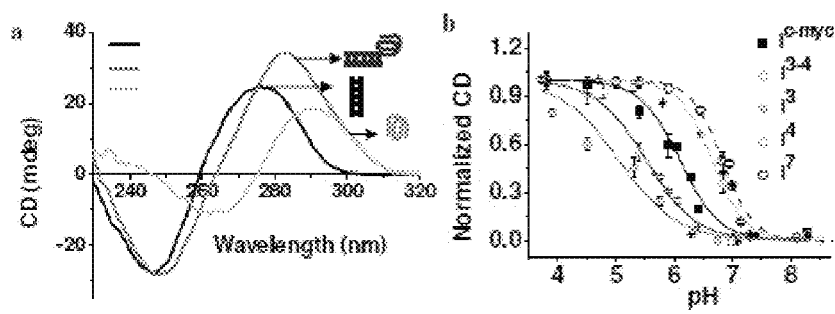

Design and Tuning of DNA pH Sensors:

The present design of DNA pH sensor which is a part of Nucleic acid assembly incorporates a 35 bp long duplex leading into a mismatched duplex at one end as shown in FIG. 1a. The pH sensor segment is a C-rich strand, shown in green (FIG. 1a), of composition $(C_nTAA)_4$ where n=2 to 7 and this is base paired with a G-rich overhang composed of $(TTAGTG)_3$, where the 'T' in italics represents a mismatch (FIG. 2).

At neutral pH, these two segments are engaged in a duplex comprising 4-5 mismatches that are deliberately incorporated in order to decrease the $T_m$ of this region. When the pH is lowered, this mismatched duplex dissociates, allowing the C-rich strand to fold into an intramolecular i-motif (FIG. 1a). To check whether this structural transition occurs in solution, circular dichroism (CD) studies on the DNA assembly at neutral and acidic pH values are carried out. CD spectroscopy on the conventional i-motif shows that this assembly adopts a linear B-DNA conformation at neutral pH, whereas at acidic pH the mismatched duplex dissociates to form an intramolecular i-motif (FIG. 3a).

Three different sequences of sensors are used in fluorescence experiments:
 (i) Cytosine stretch of 3 (i.e.: $(C3TAA)_4$; SEQ ID No. 53) known as C3.
 (ii) Cytosine stretch of 4 (i.e.: $(C4TAA)_4$; SEQ ID No. 54) known as C4.
 (iii) Cytosine stretch of 7 (i.e.: $(C7TAA)_4$; SEQ ID No. 55) known as C7.

2 sequences are explored by Circular Dichroism:
 (i) Cytosine stretch of 3 and 4 (i.e.: CCCC TAA CCC TAA)$_2$; SEQ ID No. 56) known as C3-C4 mixed.
 (ii) Nuclear hypersensitive element of C-myc gene (i.e.: CCC CA CCCT CCCCA CCC TC CCC; SEQ ID No. 57) known as C-myc.

The CD spectra of $I^4$ in phosphate buffer at about pH 8.3 showed a positive band centered at about 278 nm and a negative band centered at about 248 nm characteristic of a B-DNA duplex (FIG. 3a). However at about pH 4.0, the same assembly showed a CD where the positive and negative bands shifted to about 285 nm and about 251 nm respectively (FIG. 3a). The difference spectrum of the DNA assembly $I^4$ at about pH 4 and about pH 8.3 gives a trace that shows a positive band centered at about 288 nm and a negative band centered at about 262 nm which is consistent with the CD signature characteristic of DNA$_4$ i-motifs.

Different cellular organelles maintain their lumenal pH set point at values ranging from about pH 4.8 (lysosome) to about pH 7.1 (ER); and in order to accurately measure pH correlates associated with organelle functionality, it is important to have DNA pH sensors that span this entire pH regime. The advantage of a nucleic acid-based sensing scaffold is that sequence variation results in altered affinity of the DNA scaffold for the analyte that triggers the conformational change. Therefore, the length of the cytosine runs on the pH sensing domain of the DNA assembly which is varied from n=2 to 7 and the pH profile of the constructs are investigated by measuring the change in CD signal at 292 nm corresponding to i-motif formation as a function of pH (FIG. 3). CD spectra of about 1.5 µM Nucleic Acid Assembly in about 100 mM KCl solution of pH ranging from about pH 3.7 to about 8.5 are recorded.

A plot of the CD signal at 292 nm, as a function of pH yields an inverse sigmoidal curve indicating a pH dependent structural transition. Interestingly, it is observed that increasing the number of cytosines results in a gradual increase of the transition pH (FIG. 3b). This demonstrates tunability of pH sensitivity by tuning i-motif stability in the DNA assembly. This is consistent with the fact that increasing the cytosine tract increases the thermodynamic stability of the i-motif, and at increased pH, i-motifs composed of larger numbers of cytosine residues are sustained by a minimal number of C—C$^+$ base pairs even if C/C$^+$>1.

In order to confirm this, the pH of the structural transition is tuned by rational design, and sequence comprising C rich runs of C4-C3-C4-C3 are investigated (FIG. 2) that are predicted to show pH sensitivity intermediate between C3 and C4. Indeed, this C3-C4 mixed sequence, I$^{C3-C4}$ shows a structural transition pH intermediate between n=3 and n=4. Further a sequence such as that of the c-myc gene, I$^{C-myc}$ which has the number of cytosine residues very similar to I$^4$, but positionally varied such that formation of either an i-motif of 8 C—C$^+$ base pairs or 6 C—C$^+$ pairs is possible shows a structural transition intermediate between I$^{C3-C4}$ and I$^4$ (FIG. 3b). This clearly demonstrates tunability of pH sensitivity by tuning i-motif stability in the DNA assembly.

Figure 4:
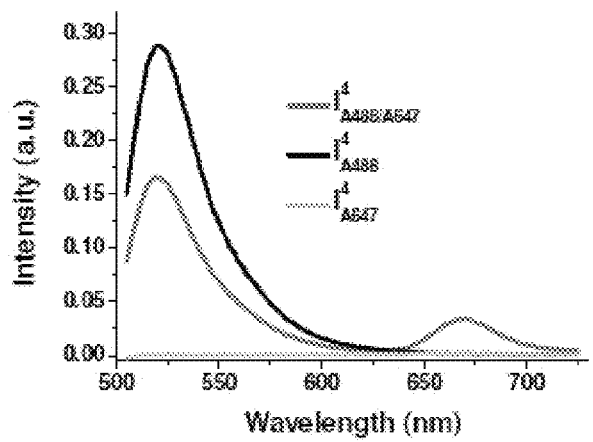

Given that the pH dependent transition is tunable, it is sought to observe whether this property is captured photonically in the corresponding DNA device functionalized with donor (Alexa 488) and acceptor (Alexa 647) fluorescent labels at the indicated locations (FIG. 1a, FIG. 4).

When fluorescence spectra of samples composed of donor only (I$^4_{A488}$), acceptor only (I$^4_{A647}$) and dual-labeled (I$^4_{A488/A647}$) Nucleic Acid Assembly at pH 5.0 are acquired, only the dual-labeled sample shows high FRET confirming i-motif folding (FIG. 4). FIG. 4 relates to steady state fluorescence measurements on Nucleic Acid Assembly. Fluorescence spectra of differently labeled Nucleic Acid Assemblies demonstrate i-motif folding. About 50 nM of labeled switch is diluted in about 20 mM phosphate buffer of about pH 5.0 containing about 100 mM KCl, incubated for about 30 min before acquiring spectra. Samples are excited at about 495 nm and fluorescence spectra is recorded from about 505 nm to about 725 nm.

Tunable nature of the Nucleic Acid Assemblies is further demonstrated by FRET. In each case, a solution of the doubly labeled assembly (I$^n_{A488/A647}$) in about 100 mM KCl at different pH values is excited at about 495 nm and the ratio of emission at about 520 and about 669 nm is plotted as a function of pH. I$^3_{A488/A647}$ yields a sigmoidal curve with a pH sensitive regime of about pH 6 to about 6.5; I$^4_{A488/A647}$ shows a pH sensitivity from pH about 6.2 to about 7 and I$^7_{A488/A647}$ shows a pH sensitive regime of about 7-7.5 (FIG. 1c). Importantly, the midpoint of the pH dependent structural transition resulted by FRET varies from pH about 6.3 (I$^3_{A488/A647}$) to about 6.6 (I$^4_{A488/A647}$) to about pH 7.2 (I$^7_{A488/A647}$) which corresponds with the lumenal pH of organelles such as trans-Golgi network (pH$_{TGN}$=about 6.0), cis-Golgi (pH$_{Golgi}$=about 6.7) and endoplasmic reticulum (pH$_{ER}$=about 7.1).

Figure 17:
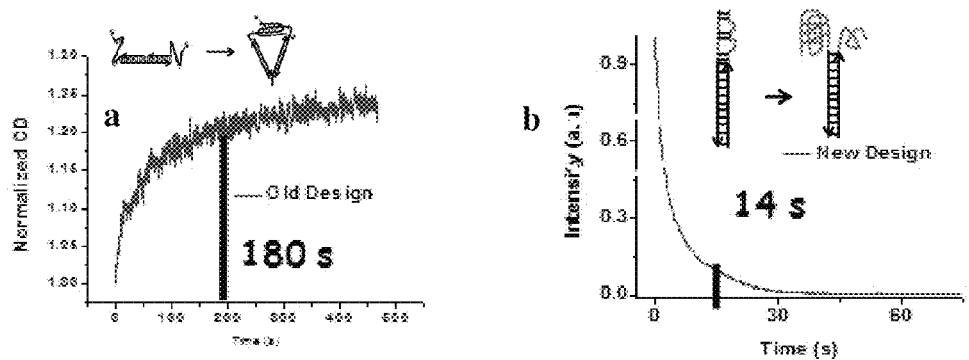
FIG. 17 depicts comparative analysis of folding kinetics between two different i-switch designs. (a) Trimeric switch, where i-motif formation is bi-molecular (Old design) and (b) Dimeric switch, where i-motif formation is unimolecular (New design).
Figure 18:
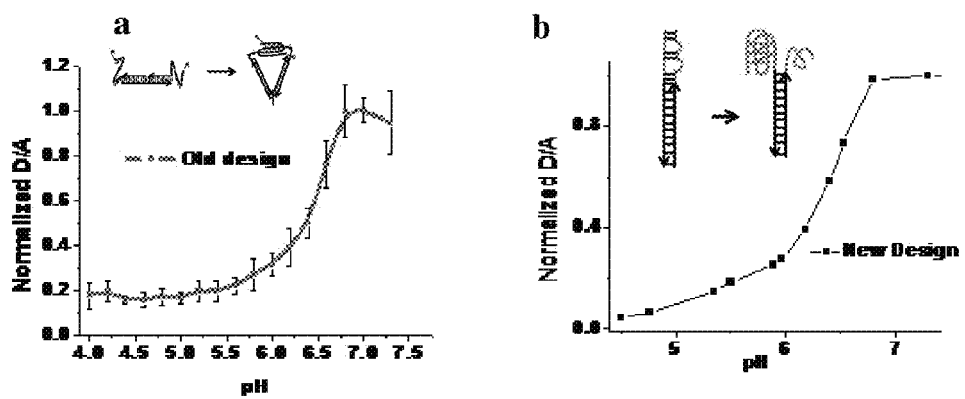
FIG. 18 depicts comparative analysis of in vitro pH profiles between two different i-switch designs. (a) Trimeric switch where i-motif formation is bi-molecular (Old design); and (b) Dimeric switch where i-motif formation is unimolecular (New design).

To assess the typical response times of these DNA assemblies, their folding times are measured at different acidic pH values by following the donor fluorescence change over time after subjecting the samples to the corresponding acidic pH jump from about pH 7.9 (FIG. 1d). The folding time of I$^3_{A488/A647}$ increases with pH and varies from about 15 s to about 100 s as the pH is changes to about 4.0 or to about 6.5 respectively. A similar trend is also observed in the case of I$^4_{A488/A647}$ where the folding time changes from about 6 s to about 100 s at pH of about 4 and about 6.7 respectively. A plot of folding time of I$^3_{A488/A647}$ and I$^4_{A488/A647}$ at different pH values is shown in FIG. 1d. Notably, the design of an intramolecularly folding I-motif based Nucleic Acid Assembly results in a significant improvement in sensor response time i.e., as fast as about 15 s from the previously reported response time of 600 sec (FIG. 17).

Example 2

Nucleic Acid Assembly Sample Preparation

In an embodiment of the present disclosure, oligonucleotides as captured in TABLE I above are dissolved in Milli-Q water to make about 200 μM stock which is aliquoted and kept at around −20° C. Depending on the purity of fluorescently labeled oligonucleotides, they are subjected to ethanol precipitation prior to use to remove any contaminating fluorophores.

About 5 μM of I'' and I''' (where n and n' are complementary strands that makes Nucleic acid assembly and mentioned in Table 1, e.g. I$^4$ assembly composed of I$^4$ and I$^{4'}$) are mixed in equimolar ratios in about 20 mM potassium phosphate buffer of desired pH containing about 100 mM KCl. The resultant solution is heated to 90° C. for about 5 minutes, cooled to the room temperature at 5° C./15 min and equilibrated at 4° C. overnight. Prior to experiment, the solution is diluted in appropriate buffer containing about 100 mM KCl unless mentioned.

Example 3

Recombinant Antibody that Binds a dsDNA Tag

In order to make DNA-based pH sensors amenable to a wide number of trafficking pathways, an artificial DNA binding protein is engineered that is grafted onto any intracellular protein of choice. This artificial DNA binding protein possesses the following desirable characteristics: (i) it binds dsDNA specifically (ii) with a high affinity (iii) is relatively small in size and (iv) does not perturb the cellular transcription program upon its expression.

Single chain variable fragments (scFv) are the minimal binding domains of immunoglobulin composed of a single polypeptide with the V fragment heavy chain (V$_H$) and light chain (V$_L$) attached sequentially by a flexible glycine-serine linker with a C-terminal His-tag and Myc-tag. They possess all the above characteristics and further are used to develop recombinant antibodies against many classes of molecules including DNA using phage display. Therefore, phage display of recombinant antibodies against the 35 base pair dsDNA handle engineered into the pH sensor assemblies to obtain high-affinity, sequence-specific protein binders to the handle domain is conducted.

Figure 5:
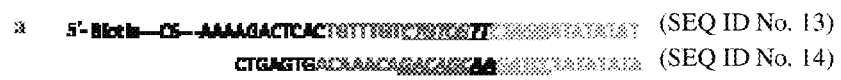
Figure 5:
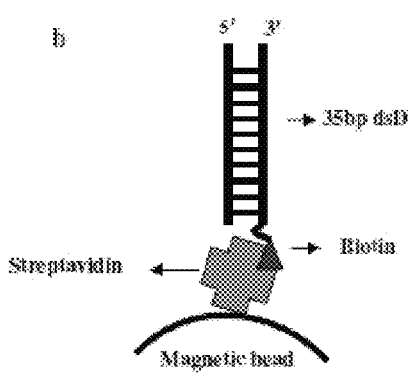
Figure 5:
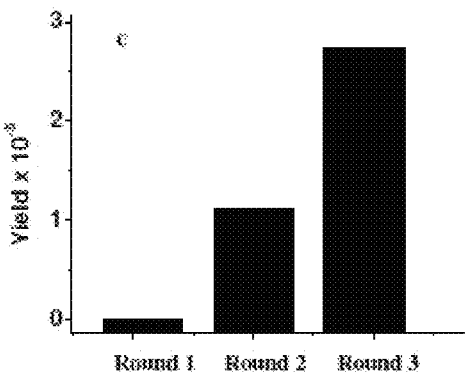

The DNA duplex or the NAA is formed by annealing the 35 bp DNA (Table 1) functionalized with biotin at the 5' end of 35 bp dsDNA that enables its immobilization on Streptavidin-coated magnetic beads that is then presented as the epitope to the scFv [Artificial Receptor] libraries (FIG. 5a,b).

Phage Display Technique to Generate Recombinant Antibodies Against DNA Duplex [NAA]:

scFv libraries (Tomlinson I and J, Geneservice, UK) that contain 10$^8$ different scFv fragments cloned in an ampicillin resistant phagemid vector are used for screening against dsDNA epitope (i.e. 35 base pair long Nucleic Acid Assembly handle, FIG. 5a). These libraries allow expression of a recombinant antibody fragment with a Myc and His tag as a protein fusion with a truncated integral phage coat protein P3 on the surface of a phage particle. Phage particles are presorbed against Streptavidin coated magnetic particles (Dynabeads, Invitrogen) in order to remove anti-Streptavidin scFvs followed by incubation with Streptavidin coated magnetic particles immobilized with dsDNA epitope or NAA (FIG. 5b). After each round of incubation, bound phage particles are collected by magnetic separation and then used to infect bacteria for amplification. Selected, amplified phage particles are isolated from TG-1 by superinfection with helper phage and used as a library for subsequent rounds of selection.

After three rounds of selection the yields of each round are compared and a gradual enrichment of a few clones over three rounds is observed (FIG. 5c). Individual clones are isolated from the output of round 3, and are expressed in a 2 mL 96-well plate (Greiner bio one) after induction with IPTG.

Following standard procedure; three rounds of progressive selection and amplification result in the enrichment of a few binders that are considered for further analysis (FIG. 5c). Randomly picked clones from the selected population are arrayed in a 96 well plate, and corresponding soluble scFvs are expressed and screened for dsDNA binders or NAA binders. Nearly 70% of screened clones display DNA binding properties coupled with negligible affinity for Streptavidin that also forms a part of the epitope during phage display but is also selected against using a pre-clearing step.

Although not the focus of the current study, the versatility of antibody phage display technique in generating anti-DNA antibodies is notable, particularly because the naïve libraries used herein have been used thus far to generate antibodies against mainly protein antigens.

Selection of Sequence-Specific scFvs:

Sequence specific scFvs are identified by dividing the 35 bp dsDNA or NAA into three regions. One region is composed of the 13 base pairs of the antigen from 3' end (known as Region 1 ($R_1$), FIG. 6a, red), the second region corresponded to base pairs 16 to 28 from 3' end (Region 2 ($R_2$), FIG. 6a, green) and third region is an overlap of regions 1 and 2 (Region M ($R_M$), FIG. 6a, blue). These three duplexes are annealed and then immobilized on three different 96-well plates. scFv supernatant of the same clones is added to the wells and incubated as described in prior art.

In order to screen for sequence specificity of binding to duplex DNA or NAA, each of the selected clones is similarly assayed by ELISA to a set of DNA bound scaffolds that are surface immobilized. These correspond to a single stranded DNA sequence comprising only the biotinylated strand of the 35 bp dsDNA (FIG. 1e, ssDNA), the 35 bp dsDNA duplex (FIG. 1e, dsDNA), and three shorter duplex regions $R_1$, $R_2$ and $R_M$ corresponding to various sections on the 35 bp dsDNA duplex (FIG. 1e). $R_1$ corresponds to a 13 bp region at the 3' terminus of the biotinylated ssDNA oligonucleotide, $R_2$ corresponds to a 13 bp region abutting $R_1$, while $R_M$ corresponds to a 13 bp region overlapping the 5' end of $R_1$ and the 3' of $R_2$ (shown in italics in FIG. 5a).

The DNA binding scFvs that show binding to the 35 bp dsDNA epitope or NAA but not the ssDNA epitope, are chosen for a further screen against the three epitopes $R_1$, $R_2$ and $R_M$. The binding efficiencies of the scFvs against $R_1$, $R_2$ and $R_M$ indicate their sequence specificity as well as narrow down the size of their respective epitopes. It is observed that 21% of the clones are specific for $R_1$ (FIG. 1f, FIG. 6b(i)), whereas 3% of clones bound $R_2$ (FIG. 6c).

Figure 6:
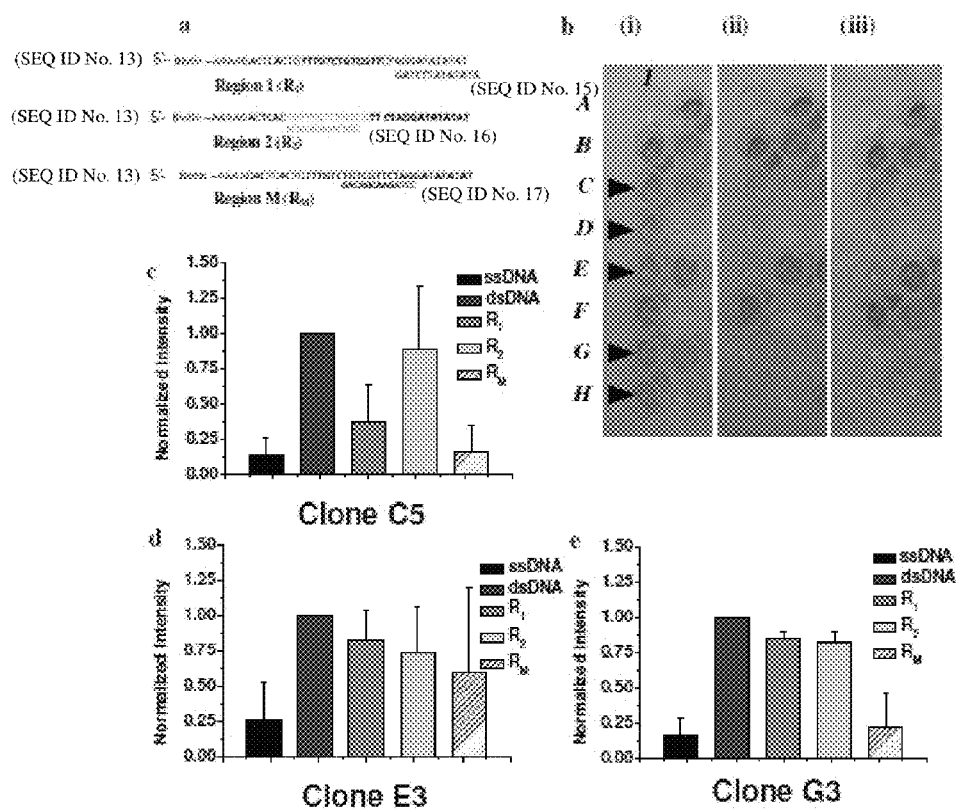

In an embodiment of the present disclosure, it is observed that most of the clones are specific for $R_1$ (FIG. 6b(i)), in that they did not bind $R_2$ (FIG. 6b(ii)) or the $R_M$ (FIG. 6b(iii)). For example, clones C1, D1, E1, G1 and H1 are distinct from each other binding to $R_1$ and no other region. Thus, it is fair to conclude that the scFvs corresponding to these clones recognize only the first 8 base pairs of the 35 bp dsDNA i.e., the sequence $d(AT)_4$. 3 clones are specific for $R_2$ (One representative clone is shown in FIG. 6c). Few clones that bind all three regions, showing no sequence specificity are also shown, which are not included for further analysis (FIG. 6d).

Sequencing of Selected scFv:

Phage display libraries Tomlinson I and J incorporate diversity in 18 residues in the complementarity determining regions (CDR), specifically H50, H52, H52a, H53, H55, H56, H58, H95, H96, H97, H98, L50, L53, L91, L92, L93, L94 and L96 (where H corresponds to the heavy chain and L corresponds to the light chain). To check the diversity at these residues of the clones that recognize a specific sequence, plasmid DNA isolated from the clones is sequenced. Sequencing by standard dideoxy method reveals some interesting features. Among 28 clones that are sequenced, 14 different sequences are present in the pool. It is also observed that of the 14 clones that are specific for $R_1$, 11 clones share the same sequence, i.e. ~78% clones express the same scFv.

Sequencing also reveals the presence of lysine, arginine, asparagine which are known for their DNA binding properties. Most of the scFvs have around 5-8 positively charged residues in their CDRs, reminiscent of other DNA binding antibodies. The most notable feature revealed by sequencing is the presence of three nearly conserved residues among 21 region specific clones, lysine at H53 (~81% clones), serine at H95 (76%) and arginine at position L92 (~85%) (FIG. 7).

Figures 7, 8:
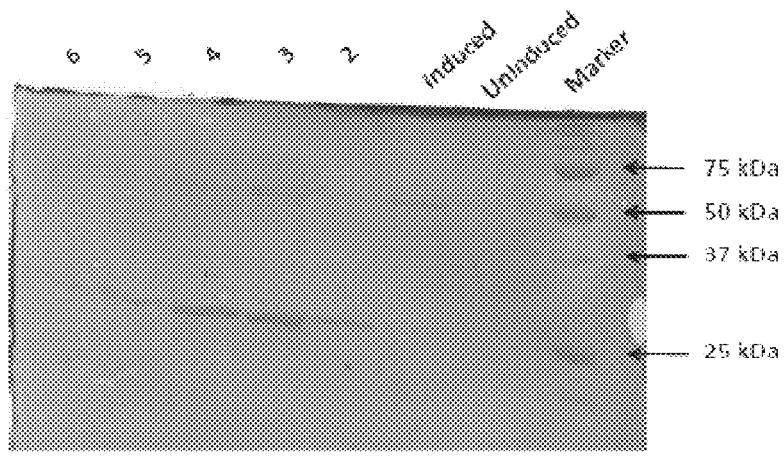

Analysis of the aligned protein sequences of these DNA-sequence specific binders reveals several positionally conserved positively charged residues in their CDRs (FIG. 7). Careful analysis also reveals that 11 out of 14 clones that are specific for $R_1$ share the same amino acid sequence (including clone C1, FIG. 1f), whereas only 2 $R_2$ specific clones share similar sequences.

scFv Expression and Purification:

The clone C1 is chosen for further studies due to its high representation in the pool that reflects its high affinity and/or production efficiency (FIG. 8). This scFv contains the bacterial pelB signal sequence at the N-terminus that secretes scFv into the periplasm where the pelB signal sequence is removed and scFv secreted into the medium. When protein is expressed in either 2×TY or M9 minimal media and subjected to a purification involving Ni-NTA or His Pur Cobalt Resin, it shows a single band near 27 kDa. When all the fractions are analyzed by the SDS-PAGE, maximum abundance is seen in fractions 2-4 (FIG. 8). These fractions are pooled and the concentration of scFv is measured by Bradford assay. A typical preparation yields about 0.5-2 mg/300 mL protein.

FIG. 8 shows scFv production and purification. Clone C1 is expressed in M9 media supplemented with about 0.1% casamino acids and about 0.2% glycerol.

Marker: Precision plus protein marker (Bio-Rad);

Un-induced: supernatant of un-induced culture;

Induced: supernatant of culture induced by about 1 mM IPTG;

2-6: fractions 2-6 collected post elution with about 500 mM imidazole.

Binding Studies with scFv and 35 Bp dsDNA Epitope or NAA:

Affinity of scFv C1 with the 35 base pair DNA duplex or NAA (FIG. 5a) is studied by ELISA in three formats that (i) use varying dsDNA concentration, (ii) use varying scFv concentration, (iii) use unlabeled dsDNA epitope as a competitor.

Figure 9:
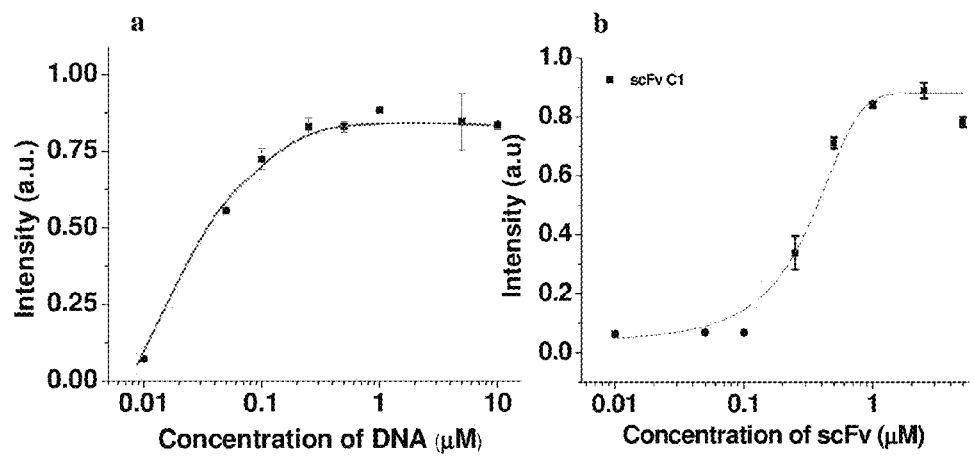
Figure 10:
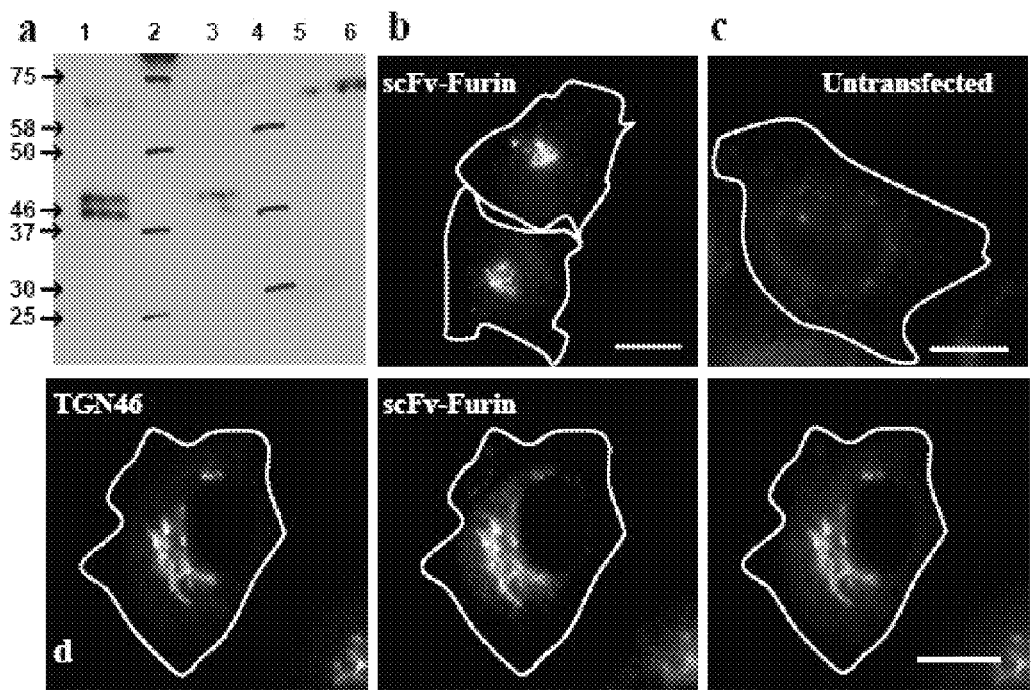
Figure 11:
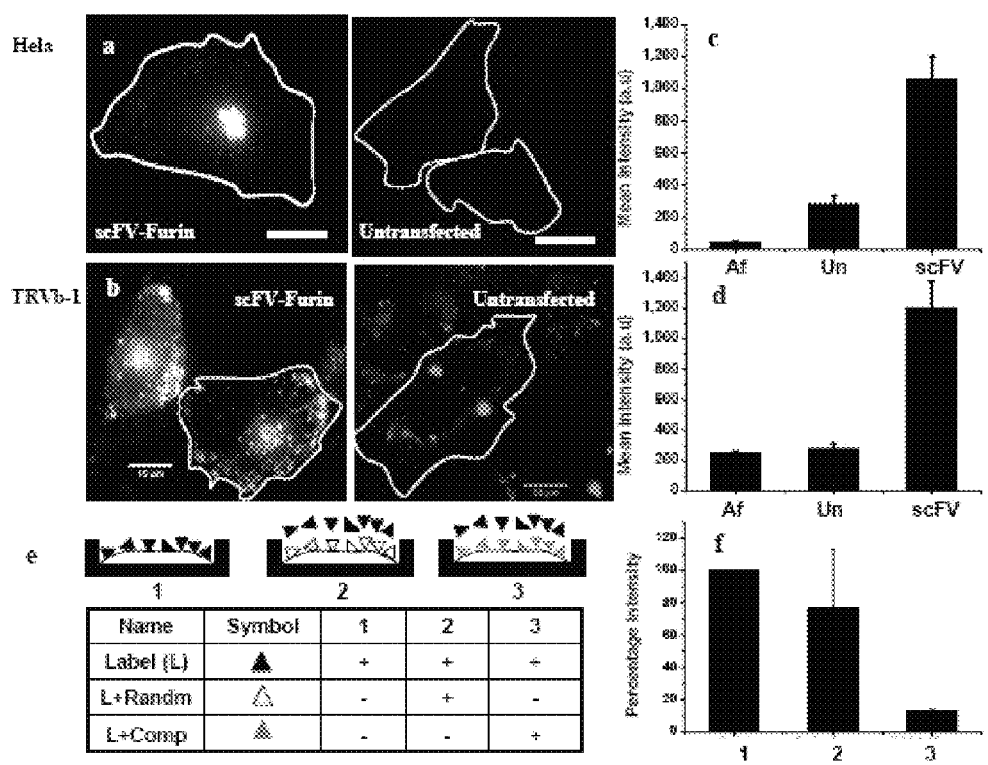

When concentration of immobilized dsDNA or NAA is varied while probing with a fixed concentration of scFv (3 µM, 100 µL), a plot of UV absorbance at 450 nm ($OD_{450}$), as a function of DNA, yields a sigmoidal curve. Normalization to the fraction of bound scFv yields an $IC_{50}$ value of 31±5.8 nM indicating a high affinity complex between scFv and DNA (FIG. 9a). When immobilized DNA amount (25 pmoles) is kept constant; scFv concentration is varied and $OD_{450}$ is plotted as a function of scFv concentration. This yields a sigmoidal curve which is fitted regression analysis to a single site binding isotherm with $IC_{50}$ of 238±67 nM (FIG. 9b).

A competition binding assay is typically performed using a fixed amount of immobilized dsDNA or NAA (25 pmoles) followed by the addition of a fixed concentration of scFv (200 nM) in the presence of an increasing concentrations of unlabeled dsDNA or NAA ($I^{comp}$, about 10 nM to about 1 µM) in solution (FIG. 1g). This assay yields an estimate of the binding affinity of scFv and dsDNA or NAA in solution. One well, with no added competitor serves as a normalization factor for the 100% binding event. The concentration of competitor where 50% reduction in binding is observed and gives measure of the inverse of the relative binding constant which is found to be about $1.25 \times 10^7 M^{-1}$ (i.e, $K_D=80$ nM). This confirms that scFv has a nanomolar affinity towards a given sequence of $d(AT)_4$.

Example 4

Selection of NAA or dsDUPLEX Specific scFvs dsDNA epitope or NAA is prepared by annealing about 50 µM ssDNA and ssDNA' in 1×PBS supplemented with about 100 mM KCl. Nonspecific binders (in particular anti-Streptavidin scFvs) are removed from the library by incubating scFvs displayed on the surface of phage with Streptavidin-coated magnetic beads alone. Rest of the phage display screen is adapted from the Tomlinson protocol provided by the library manufacturer and carried out as described in prior art. This protocol provides a method to screen a dsDNA specific scFv.

Example 5

ELISA for Screening Positive Clones

Approximately 96 colonies from the final round of selection are screened by ELISA against dsDNA or NAA. Individual colonies from last round of selection are grown into a 96 well plate till $OD_{600\ nm}$ reaches approximately 0.9 and induced with about 1 mM IPTG. Cultures are grown at about 30° C. overnight (~16 hours) for the expression of soluble scFvs and soup containing scFvs is transferred onto Streptavidin-conjugated 96-well plate containing immobilized dsDNA or NAA to carry out standard ELISA assays. Typically about 150 µL of scFv soup containing 1 in 1500 dilutions of anti-cMyc antibody (clone 9E10, Millipore)/anti His-tag antibody (clone His-1, Sigma,) is added to each well and incubated for about 1.5 hours with gentle shaking Goat anti-mouse secondary antibody conjugated to HRP (1 in 1000 dilution, Invitrogen) is used to detect anti-cMyc antibody bound to plate through scFv which binds to ds DNA immobilized on the plate.

Approximately 96 colonies from the final round of selection are screened by ELISA against dsDNA or NAA. In order to check the sequence specificity of the positive clones, scFvs are subjected to another round of ELISA assay against various DNA epitopes. The epitopes used are ssDNA (5'-biotinylated oligo only), dsDNA (duplex DNA used as antigen) and various parts of this dsDNA (e.g. Region 1 as $R_1$, region 2 as $R_2$ and region middle as $R_M$). After immobilization of these targets, ELISA assay is carried out as mentioned earlier. This assay identifies and differentiates the dsDNA binding scFvs from other non interacting scFvs.

Example 6

Sequencing of dsDNA or NAA Specific Clones

About 30 clones showing binding to dsDNA or NAA are chosen for sequencing. Individual clones are grown overnight and subjected to a plasmid DNA isolation using Nucleospin Plasmid (Macharey-Nagel, Germany) miniprep Kit. Sequencing is performed using a standard dideoxy sequencing method using a specific primer pHen Seq (5'-CTATGCG-GCCCCATTCA-3'; SEQ ID No. 58). This protocol provides sequence of the scFvs which is used further to generate AIM.

Example 7

Determination of Binding Constants

The affinity and specificity of scFv is analyzed by ELISA after purifying the scFv using protocol described in prior art. Streptavidin-coated 96-well plate is incubated with dsDNA epitope used for screening in 5×SSCT (75 mM Sodium citrate, 750 mM NaCl+0.05% Tween-20) for about 1.5 hours for immobilization of dsDNA or NAA onto the Streptavidin-coated 96-well plate. This is followed by incubation with a mixture of serial dilutions of purified scFv and anti myc-tag antibody (1 in 1000 dilution) for 1.5 hours at room temperature.

For competition experiments, dsDNA immobilized onto Streptavidin-coated 96-well plate is incubated with the mixture of competing nucleic acid, purified scFv (250-300 nM) and anti myc-tag antibody (1 in 1000 dilution) for about 1.5 hours at room temperature. The wells are then washed briefly in 1 liter PBST (1×PBS+0.1% Tween-20) bath before the addition of the secondary antibody conjugated to HRP. Bound scFvs are detected by addition of $TMB/H_2O_2$ and OD at 450 nm is recorded and normalized with respect to the well where no competitor is added.

Example 8

Cloning of scFv with Furin Cytoplasmic Domain

Plasmid expressing chimeric forms of Furin is obtained from Dr Michael Marks. This plasmid contains lumenal and trans-membrane domains of human Interleukin receptor beta chain (TAC) with cytoplasmic tail of Furin. EGFP (Enhanced Green Fluorescent Protein) from EGFP-N2 backbone is removed by digestion of NheI and NotI (FIG. 21) and cytoplasmic tail of Furin and Lumenal TAC domain is introduced by cutting parent plasmid by the same enzymes and re-ligating it to the N2 backbone. Lumenal domain of TAC is cloned between EcoR1 and BglII site and same restriction enzymes are used to remove this domain.

scFv fused with signal sequence of Furin (ssFurin) is PCR amplified using two primers that contain EcoR1 and BamH1 restriction sites to yield ssFurin-scFv chimera. This PCR product is gel purified and digested using EcoR1 and BamH1 and ligated to EcoR1 and BglII digested N2 backbone containing cytoplasmic domain of Furin. Colonies are screened for positive clones that contain ssFurin-scFv-Furin. Sequences of the positive clones are finally confirmed by sequencing.

Figure 19:
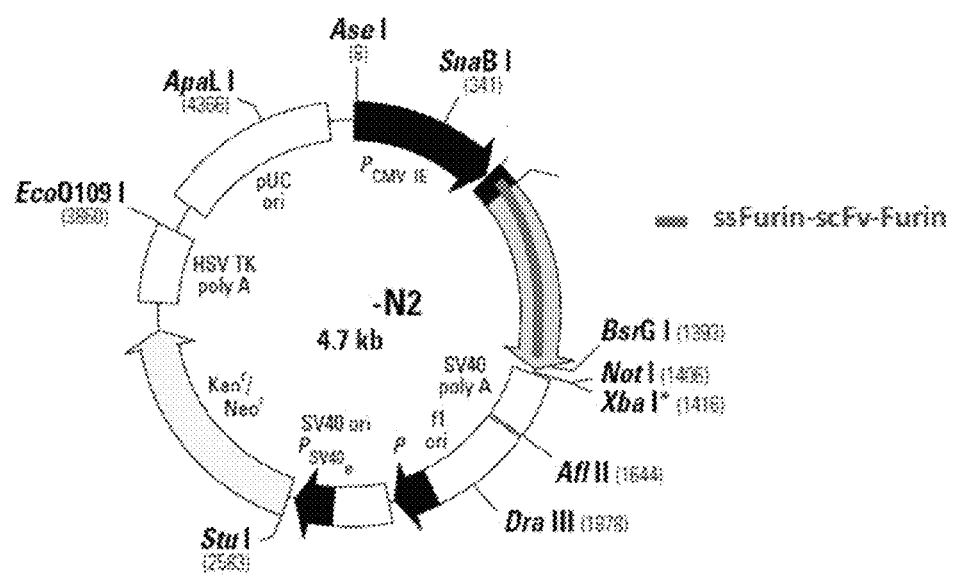
FIG. 19 depicts Expression vector based on N2 backbone; expressing a Chimeric protein consisting of signal sequence of Furin (ssFurin), scFv and cytoplasmic domain of Furin. Blue line represents full length ssFurin-scFv-Furin which is 1257 nucleotides long, cloned between endogenous Nhe1 and Not1 sites.

FIG. 19 describes vector based on N2 backbone expressing a Chimeric protein consists of signal sequence of Furin (ssFurin)—scFv and cytoplasmic domain of Furin.

Example 9

Cell Culture and Transfection

Three different cell lines are used.
(i) HeLa Cells,
(ii) TRVb-1 (Chinese Hamstar Ovary (CHO) cells expressing Human Transferrin receptor (HTfR), and
(iii) IA2.2 cells (CHO cells expressing HTfR and Folate receptor)

HeLa cells are cultured in Dulbecco's Modified Eagle's medium/F-12 (1:1) (Invitrogen Corporation, USA) containing about 10% heat inactivated Fetal Bovine Serum (FBS) (Invitrogen Corporation, USA), about 100 μg/mL streptomycin and about 100 U/mL penicillin (Invitrogen Corporation, USA).

TRVb-1 cells are a CHO cell line which lacks endogenous transferrin receptors but stably expresses the human Transferrin receptor are cultured in Ham's-F12 media (HF-12, Himedia, India) containing about 10% heat inactivated FBS, about 100 μg/mL streptomycin and about 100 U/mL penicillin with about 200 μg/mL G418 (Sigma) to ensure maintenance of Transferrin receptor.

For transient transfections, cells are plated at >50% density onto coverslip bottomed 35 mm dish and about 24 hours post plating, cells are washed and incubated for about 30 min in Opti-Mem at about 37° C. About 1 μg of DNA is diluted in about 100 μL Opti-Mem in a tube and in a separate tube, about 3 μL of Lipofectamine™ 2000 was diluted to 100 μL in same Opti-Mem. After 5 min incubation, both solutions are mixed and incubated for about 30 min at Room Temperature. About 200 ng (200 μL) of transfection mixture is introduced to the cells and incubated for about 3 hours at 37° C. Transfection mixture is removed after about 3 hours, complete media is added and incubated for about 20-24 hours. Cells are imaged 24 hours after transfection. This protocol expresses the AIM at the plasma membrane of any given cell type.

Example 10

Expression of scFv-Furin Chimera in HeLa Cells

In order to determine whether the above scFv acts as an artificial receptor that recognizes the Nucleic acid assembly and traffic the latter specifically inside cells, a scFv fusion of Furin is created, which is a protein that traffics from the plasma membrane via a retrograde endocytic pathway. Furin is an endoprotease that is expressed predominantly in the TGN and shuttles between plasma membrane and TGN via this retrograde endocytic pathway. Its cytoplasmic C-terminus is responsible for its correct retrograde trafficking from the plasma membrane. Therefore an N-terminal fusion of the scFv with Furin (scFv-Furin) is made, so that the scFv is presented towards the extracellular milieu when Furin is present at the plasma membrane.

Figure 12:
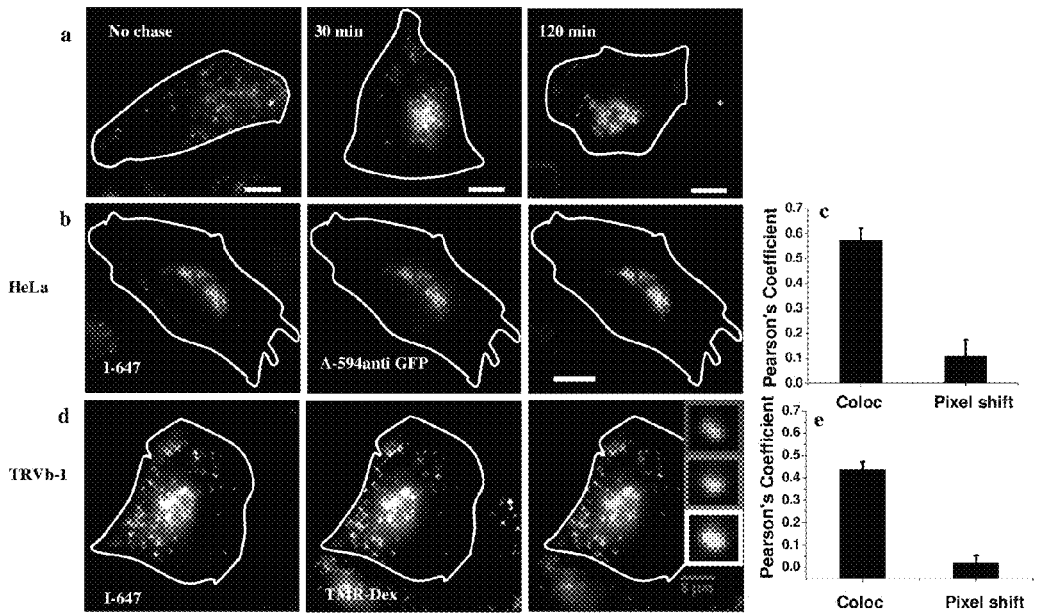

This chosen topology is compatible with redox conditions required for proper scFv folding and function; as antibodies are secreted naturally by vertebrates and during phage display by *E. coli* in oxidizing conditions. a priori any attenuation of scFv binding to the DNA handle is not expected. Thus the scFv acts as an artificial receptor for the Nucleic acid assembly that is ferried by retrogradely trafficking scFv-Furin when the fusion is expressed in cellulo.

To check expression of scFv-Furin chimera in HeLa cells, cells are transfected with scFv-Furin and about 24 hours post transfection, the cells are lysed, total protein is isolated, resolved on SDS-PAGE and probed with anti-His tag antibody.

scFv-Furin shows two closely spaced bands near the expected size (~43-45 kDa) with negligible cross reactivity towards both positive and negative controls (FIG. 10*a*).

Further, the observation of two closely spaced bands for scFv-Furin mimics that seen with endogenous Furin which is characteristic of Furin maturation. This indicates that the scFv-Furin fusion maturation recapitulates that of endogenous Furin.

In order to study its localization within the cell, immunofluorescence studies are carried out on cells expressing scFv-Furin. Since the scFv incorporates a His tag and endogenous Furin is predominantly localized in the TGN, co-localization studies with an anti-His tag antibody and a TGN marker such as anti-TGN 46 are performed. HeLa cells expressing scFv-Furin show a staining pattern consistent with scFv resident in tubular compartments present in the perinuclear region as well as in proximal small vesicles whereas untransfected controls show only non-specific background staining (FIG. 10*b,c*). When scFv-Furin expressing cells are co-stained with anti-TGN46 antibody and anti-His Tag antibody, they show perfect co-localization (FIG. 10*d*), indicating that the expression and localization of scFv-Furin is not disrupted due to presence of the scFv domain at the N-terminus of Furin.

Example 11 scFv Acts as an Artificial Receptor for Nucleic Acid Assembly

Experiments are conducted to confirm that the scFv domain is capable of recognizing and endocytosing Nucleic acid assembly from the extracellular milieu, scFv-Furin expressing HeLa cells are incubated with about 500 nM $I^4_{A488/A647}$ in the external medium for about 1 hour, washed, chased for about 10 min to about 3 hours and imaged (FIG. 11*a*).

At chase times<30 min, it is seen that $I^4_{A488/A647}$ is distributed in numerous small punctuate vesicles throughout the cytoplasm that are gradually concentrated into a tubular compartment occupying the perinuclear region over 3 hours (FIG. 12*a*). This uptake is absent in untransfected or mock transfected cells (FIG. 11*a,c*). These findings are recapitulated when the same experiment is performed on TRVb-1 cells transfected with scFv-Furin, indicating that this uptake by scFv-Furin is not cell type specific (FIG. 11*b,d*).

Cumulatively this demonstrates that the uptake of $I^4_{A488/A647}$ is specific to the presence of the scFv-Furin. In order to check whether uptake by the scFv-Furin is specific to the instant DNA assembly, a competition assay is carried out. Endocytic uptake in HeLa cells expressing scFv-Furin is measured as described for $I^4_{A488/A647}$ alone and in the presence of 50 folds excess of a random, non competitive duplex DNA sequence. It is seen that uptake of $I^4_{A488/A647}$ remains unaffected (FIG. 11*e,f*). However when the same experiment is carried out in the presence of 50 fold excess of $I^{comp}$, uptake is dramatically decreased indicating that $I^{comp}$ had sequence specifically competed out $I^4_{A488/A647}$. This confirms that the scFv-Furin chimera acts as an artificial receptor specifically for the Nucleic acid assembly sequence containing the 8 base pair tag $d(AT)_4$.

Example 12

Nucleic Acid Assembly Marks Retrogradely Trafficking scFv-Furin

Furin is predominantly present in the Trans Golgi Network (TGN), of which a small population shuttles between the plasma membrane and TGN via the sorting endosome and late endosome. To check whether Nucleic acid assembly endocytosis is mediated by scFv-Furin, an antibody uptake assay is performed. HeLa cells are co-transfected with scFv-Furin and EGFP-Furin (FIG. 12b). 24 hours post transfection, these cells are pulsed with fluorescently labeled anti-GFP antibody and $I^4_{A488/A647}$, chased for 3 hours and imaged. It is seen that anti-GFP antibody and $I^4_{A488/A647}$ are co-localized in live as well as fixed cells confirming that $I^4_{A488/A647}$ uptake is Furin mediated (FIG. 12 b,c).

Figure 13:
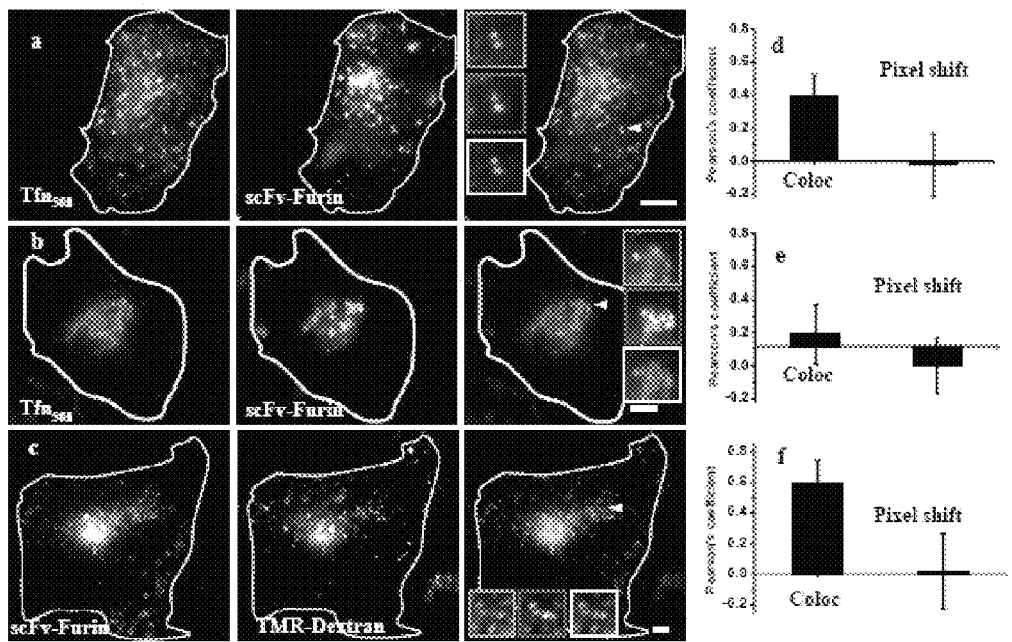

To determine whether the Nucleic acid assembly marks the Furin retrograde pathway, co-localization experiments with molecular markers of sorting endosome and late endosome are performed. First, the sorting endosomes in the scFv-Furin expressing HeLa cells are labeled with a 10 min pulse containing a cocktail of Alexa 568 labeled Transferrin ($Tfn_{568}$) and $I^4_{A488/A647}$ and imaged. It is observed that $Tfn_{568}$ and $I^4_{A488/A647}$ show significant co-localization indicating that after endocytosis, most of the Nucleic acid assembly is resident in sorting endosome (FIG. 13 a,d). However when chased for about 2 hours, this co-localization is markedly reduced indicating that the Nucleic acid assembly has trafficked forward from the sorting endosome (FIG. 13 b,e).

In order to check the identity of the compartments at the 2 hour timepoint, scFv expressing HeLa cells are labeled with a mixture of $I^4_{A488/A647}$ and TMR-Dextran. It is known that the TMR-Dextran marks the late endosome at the 2 hour time point and that it co-localizes with an antibody against the N-terminal domain of a Furin chimera that is resident at the late endosome at 2 hours.

scFv-Furin expressing TRVb-1 cells and HeLa cells are labeled with $I^4_{A488/A647}$ and TMR dextran for about 1.5 hours, washed, chased for about 3 hours and imaged. At this time point $I^4_{A488/A647}$ and TMR dextran show significant co-localization (FIG. 12 d, e and FIG. 13 c,f respectively) indicating that $I^4_{A488/A647}$ has trafficked from sorting endosome into the late endosome, characteristic of Furin mediated retrograde trafficking.

Co-localization studies of the Nucleic acid assembly with labeled Transferrin and TMR dextran show that upon retrograde traffic, the DNA pH sensor accumulates in the sorting endosome at t=10 min and post 1 hour, it is trafficked to the late endosomes in multiple cell lines. This is consistent with the retrograde trafficking of endogenous Furin known in the prior art. Tracking retrograde trafficking of EGFP-Furin and scFv-Furin compartments by fluorescently labeled anti-GFP and $I^4_{A488/A647}$ reveals that the Nucleic Acid Assembly marks the retrograde Furin endocytic pathway qualitatively and quantitatively.

Figure 14:
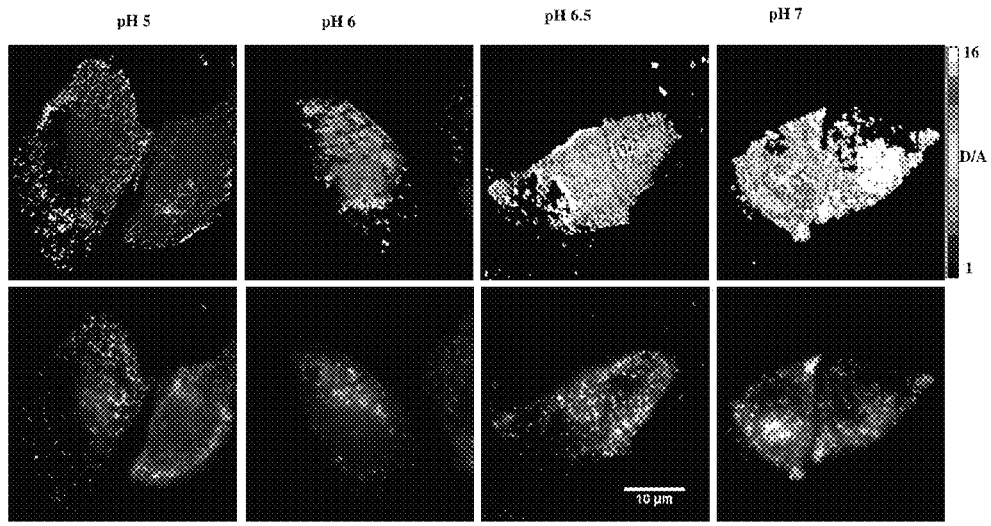

Clamping of Nucleic Acid Assembly Internalized HeLa Cells at Different pH:

scFv expressing HeLa cells are labeled with about 500 nM $I^4_{A488/A647}$ for about 15-30 minutes at 37° C. in complete media. Cells are washed and briefly fixed for about 2 min in ice using about 2% paraformaldehyde. Cells are pH clamped using clamping buffer containing about 25-40 µM nigericin. Cells are imaged in a widefield microscope after exciting at 488 nm and imaging at 520 nm (D) and 669 nm (A). D and A images are aligned and a binary image is created by dividing D images by A images. This binary D/A image is further pseudocolored in ImageJ to provide a spatial pH map of cells clamped at indicated pH values. Due to high FRET, at low pH, cells show uniformly lower D/A which concomitantly increases to higher D/A value as value of clamping buffer pH increases (FIG. 14).

Example 13

In Cellulo Performance of the Nucleic Acid Assembly

Prior to spatio-temporal pH mapping with the new family of Nucleic acid assemblies, it is important to see whether the function of the Nucleic acid assembly is affected in cellulo post-complexation with its artificial receptor. Therefore, pH clamping experiments are carried out. scFv-Furin expressing HeLa cells are labeled with $I^n_{A488/A647}$ (n=3 and 4) for about 2 hours, washed and fixed briefly for about 2 min in ice using about 2% PFA. These cells are then incubated in clamping buffers of known pH values containing about 25-40 µM Nigericin.

Figure 15:
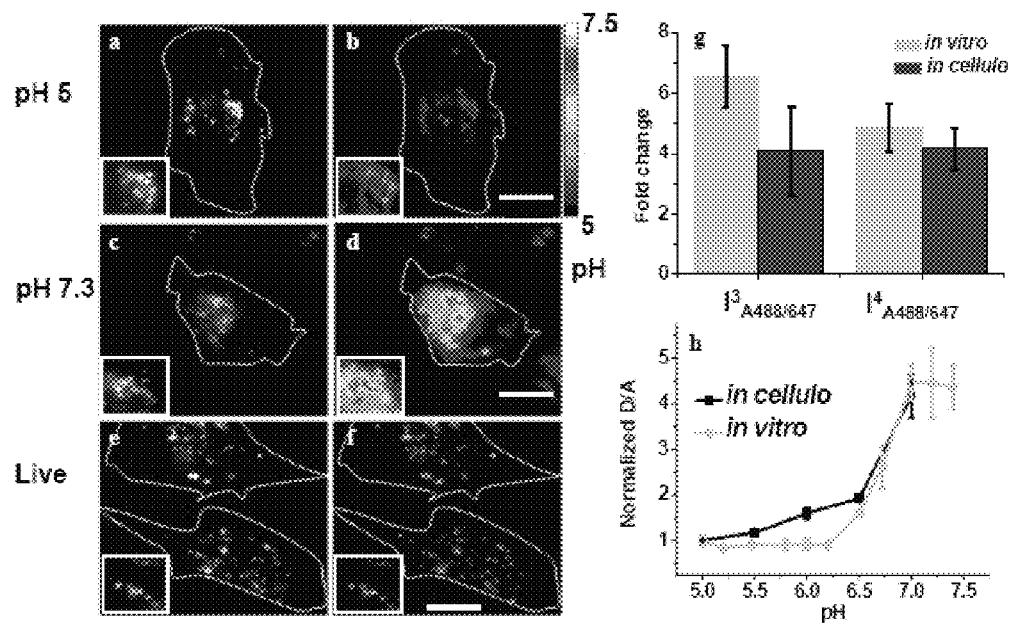

Cells are then imaged in a widefield microscope after about 40 min of incubation in clamping buffer of the indicated pH, excited at 488 nm and images are recorded at 520 nm (Donor, D image) and 669 nm (Acceptor, A image). A ratio of the image in the D channel and A channel results a binary image that is pseudocolored as a heat map using ImageJ (FIG. 14). Even qualitatively, the difference in overall D/A of endosomes in cells clamped at pH about 5.0 and pH about 7.3 is clearly evident (FIG. 14 and FIG. 15 b, d, f).

The corresponding image in live cells shows the characteristic heterogeneity in pH at chase times (FIG. 15e, f). The fold change in D/A values for two different pH sensors $I^3_{A488/A647}$ and $I^4_{A488/A647}$ in cellulo indicates that sensor performance and integrity are uncompromised (FIG. 15g). To check the performance of $I^4_{A488/A647}$ over a range of pH, $I^4_{A488/A647}$ labeled endosomes are clamped at the indicated pH values and D/A as a function of pH is plotted to yield the pH calibration curve. When overlaid, the in vitro and the in cellulo pH calibration curves show good correspondence (FIG. 15h) indicating that the performance of the DNA pH sensor is not affected post-recognition by its artificial receptor.

Example 14

Nucleic Acid Assembly Reveals pH Gradient Inside Cells

Figure 16:
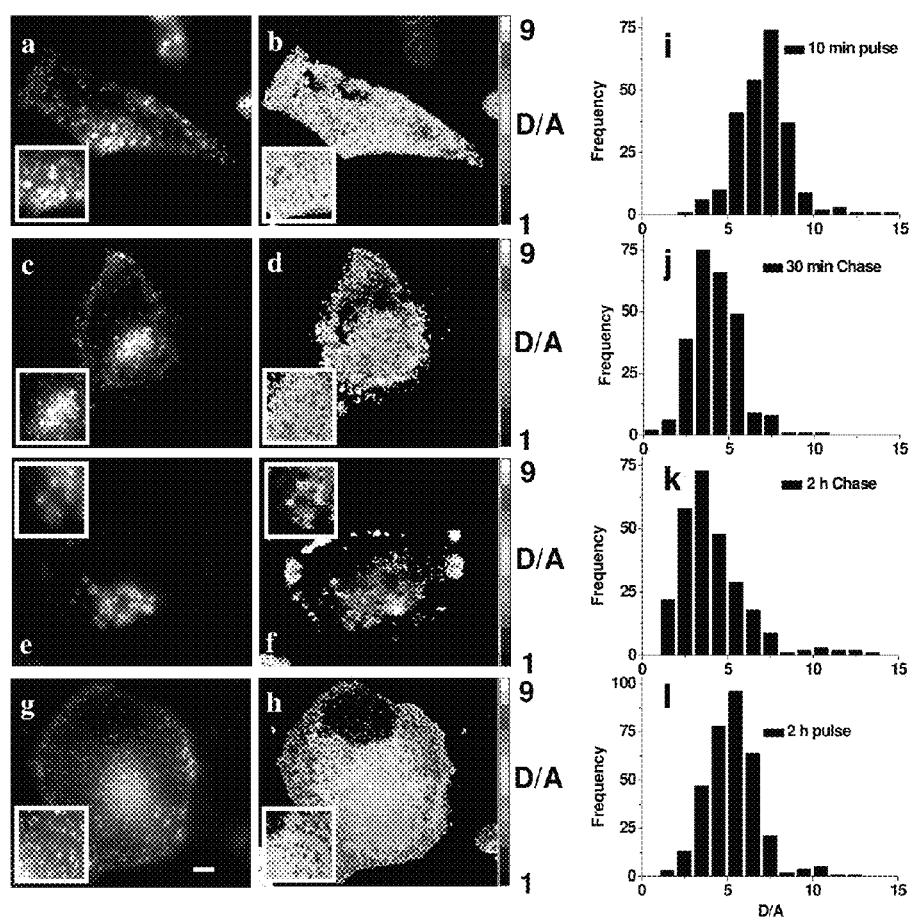

To demonstrate the utility of the present aspect, spatial and temporal pH mapping is carried out in HeLa cells in two different ways. In the first method, scFv-Furin expressing HeLa cells are pulsed with $I^4_{A488/A647}$ for about 10 min which is shown to label sorting endosomes, washed and imaged. The pH map at this time point shows a uniform distribution pH across all endosomes which leads to a mean pH spread of 6.4±0.27 characteristic of sorting endosomes (FIG. 16a,b,i).

When cells are chased for more than 30 min, an accumulation of the Nucleic acid assembly is observed in perinuclear region. The pH map at this time point reveals a distinct shift with the overall pH distribution decreasing significantly with a pH spread of 5.4±0.56 characteristic of late endosomes (FIG. 16c,d,j).

Given the high precision and sensitivity of the DNA-based pH sensor over this pH regime, a complementary method to label cells that provides a spatial pH map of the set of all retrogradely trafficking scFv-Furin compartments across cell is used. In this method, scFv-Furin expressing HeLa cells are labeled for about 2 hours to achieve steady state labeling where all scFv-Furin containing endosomes are expected to be labeled. FIG. 16f represents the pH map of labeled endosomes which shows a clear spatial correlate of endosomes with similar acidities, indicating the ability of the Nucleic Acid Assembly to differentiate between sorting and late endosomes on the Furin pathway and also their relative spatial intracellular locations.

Example 15

Circular Dichroism Spectroscopy

All CD experiments are performed on a JASCO J-815 spectrophotometer equipped with a temperature controller. Nucleic acid assembly stock solution, prepared in pH 5.0 water containing about 100 mM KCl, is given a pH jump to a desired pH by addition of about 25 µL of 1 M buffer of appropriate pH. The sample is equilibrated for about 30 min to about 60 min prior to acquisition of spectra and transferred to a 1 cm quartz cuvette. CD spectra are recorded from 320 nm to 200 nm with 1 nm/s bandwidth and 0.25 s response time. An average of 3 successive scans is acquired. CD signal at 292 nm at different pH is recorded and normalised to 0-1 by taking CD signal at closed state as $Y_{max}$ and CD at open state as $Y_{min}$ and using the formula given below in Origin 8.

$$Y = \frac{Y - Y_{min}}{Y_{max} - Y_{min}}$$

Mean of CD signal at 292 nm from two independent experiments and their SD are plotted for each pH value. This protocol provides a platform to generate a range of pH sensors with varying transition pH.

Example 16

Steady State and Ratiometric Measurements

About 5 µM stock of fluorescently labelled Nucleic Acid Assembly sample is prepared in about 20 mM phosphate buffer pH 5.5, supplemented with about 100 mM KCl ($I^n_{A488}$, $I^4_{A647}$ are used to prepare samples). Solutions of Nucleic Acid Assembly at different pH are made by diluting about 1 µL of about 5 µM stock samples into 99 µL of 1× clamping buffer of desired pH. All samples are vortexed and equilibrated for about 30 min at room temperature.

The experiments are performed in a widefield microscope. The cover-slips containing about 50 µL samples of different pH are excited at 488 nm in a widefield microscope and emission images are acquired using 520 nm (Donor, D channel) and 669 nm (Acceptor, A channel). An in vitro pH calibration curve is obtained by plotting the ratio of donor intensity (D) at 520 nm by acceptor intensity (A) at 669 nm as a function of pH. Mean of D/A from two independent experiments and their SD are plotted for each pH value. This protocol provides the platform to generate a range of pH sensor with varying transition pH.

Example 17

Kinetics of Folding of Nucleic Acid Assembly

Folding kinetics of different Nucleic Acid Assemblies are measured in FluoroMax-4 Spectrofluorometer (Horiba Jovin Yvon, Japan) by monitoring fluorescence change after a pH jump from pH 7.9. About 5 µM dual-labeled Nucleic Acid Assembly is annealed in 50 mM pH 7.9 MES buffer containing about 100 mM KCl. About 2 µL of this sample is diluted to about 150 µL in the same buffer and transferred into a fluorescence cuvette (Hellma, Germany). Fluorescence emission at 520 nm is followed over time after a pH jump by addition of various amounts of 1 N HCl. Typically, about 25 µL of HCl is needed for a pH jump to pH about 4.5-4.7 from pH about 7.9 and after completion of the run, exact pH of the solution is measured and reported. This protocol provides folding times of a given I-switch at different pH values.

Example 18

Immunoblot and Immunofluorescence Analysis

HeLa cells ($10^6$) are transfected using ssFurin-scFv-Furin and 24 hours post transfection, cells are collected and washed twice with PBS. Untransfected cells and EGFP-Furin transfected cells are used as negative control and positive control for transfection respectively. Whole cell lysates are prepared by addition of about 100 µL RIPA buffer followed by incubation for about 1.5 hours at 4° C. An aliquot of each lysate is subjected to SDS-PAGE and transferred to nitrocellulose using standard protocol. The nitrocellulose membrane is incubated with a 1:1000 dilution of anti-His-tag antibody (clone His-1, Sigma). Binding of primary antibody is detected by the ECL method (Pierce).

For immunofluorescence staining, scFv-Furin expressing HeLa cells are fixed with about 4% paraformaldehyde for about 10 minutes on ice. To detect intracellular antigens they are permeabilized with about 0.1% Saponin (Sigma) in M1 buffer and stained with rabbit anti-TGN46 antibody (Abcam) and mouse anti His-tag antibodies (Sigma) followed by goat anti rabbit-Cy3 conjugated (Abcam) and goat anti mouse-FITC conjugated secondary antibodies (EMD bioscience) for 1 hour respectively. This experiment confirms full length expression of AIM at the TGN.

Example 19

Fluorescence Staining Methods scFv-Furin expressing mammalian cells like HeLa/TRVb-1 cells are washed with M1 buffer three times prior to labeling. Cells are incubated with endocytic tracers for indicated times in labeling medium (HF-12 or DMEM, 10% serum, antibiotics). For Nucleic Acid Assembly labeling, $I^{3/4}_{A488/A647}$ is diluted in labeling media to final concentration of about 500 nM and incubated for different times at 37° C.

For labeling late endosomes, cells are incubated with $I^4_{A488/A647}$ and about 4 mg/mL TMR dextran in labeling media at 37° C. for 1.5 h. Sorting endosomes are labeled by 100 µg/mL Alexa-568 labeled, human-holo Transferrin after incubating HeLa cells at 37° C. for about 10 mins. After incubation, excess endocytic tracers are washed off using M1 and chased for indicated times at 37° C. in complete media.

For antibody uptake assay, cells are co-transfected with scFv-Furin and EGFP-Furin and 24 hours after transfection, cells are labeled with Alexa 594 conjugated rabbit anti-GFP antibody (Invitrogen, 1 in 50 dilution) and $I^{3/4}_{A488/A647}$ in labeling media for 1 hour, washed with M1 followed by a long chase for about 3 hours at 37° C. Cells are washed three times with M1 and fixed with about 4% PFA in M1 for about 10 min at room temperature.

For competition assay with unlabeled dsDNA, scFv-Furin expressing HeLa cells are labeled with about 500 nM $I^4_{A488/A647}$ in HBSS buffer for 1 hour at room temperature in presence of (1) No exogenously added DNA, (2) in presence of 25 µM random sequence DNA ($I^{non\ comp}$), (3) in presence of 25 µM $I^{comp}$ and chased for 3 hours in complete media.

Cells are washed and imaged in a widefield microscope and perinuclear fluorescence is quantified and presented as percentage intensity internalized after normalizing the data with (1). In a complementary method, cells are labeled with (1), (2) and (3) in complete media at 37° C. for about 30 min which provides similar results.

Example 20

Measurement of pH in Sorting Endosomes and Late Endosomes scFv-Furin expressing HeLa cells are labelled with about 500 nM $I^{3/4}_{A488/A647}$ in complete media for indicated times at 37° C. Cells are incubated on ice and briefly fixed by addition of about 2% PFA for 1 min in M1. Intracellular pH gradient is abolished by addition of about 25-40 µM nigericin in different pH clamping buffer ranging from 5.0 to 7.5 for about 40 min. The cells are kept in this medium until imaging, and the fluorescence ratio of donor (D, 520 nm) image to acceptor (A, 669 nm) image at different equilibrated pHs are calculated in individual endosomes after exciting at 488 nm.

The mean from the distribution of D to A ratio of individual endosome are obtained at different pH values and plotted to obtain a calibration curve. The pH of sorting endosomes and late endosomes are estimated after labeling respective compartments with $I^4_{A488/A647}$. D to A ratios is used to estimate the pH value from to the calibration curve.

The in cellulo pH calibration curve of the Nucleic Acid Assembly post complexation with and post trafficking by scFv-Furin shows remarkable correspondence with the in vitro protein-free Nucleic Acid Assembly. The fold change in D/A ratio, which is a measure of sensor performance, shows an in cellulo fold change of 4.1±0.7 and 4.0±1.7 for $I^4_{A488/647}$ and $I^3_{A488/647}$ similar to their in vitro values (4.8±0.8 and 6.5±1.02 respectively). This suggests that recognition of the duplex 'handle' region of the sensor by the scFv domain in cellulo does not alter the pH sensing characteristics of the DNA sensor. This is consistent with the modular nature of the nucleic acid scaffold of the DNA pH sensor where protein binding at a remote site is independent of the functionality due to a conformational change at a distal site.

Example 21

Image Acquisition and Analysis

Wide-field images are collected using Nikon eclipse Ti—U microscope (Nikon Japan) inverted microscope equipped with 60×, 1.4 NA objective, a metal halide illuminator (Lumen Dynamics, Ontario, Canada), and a cooled charge-coupled device (CCD) camera (Cascade II-512, Photometrics, Tucson, Ariz., USA) controlled by MetaMorph software (Molecular Devices, Downingtown, Pa.). Optimized dichroics, excitation, and emission filters are used as described in prior art. For pH measurements, cells are imaged in two channels, (i) donor channel by exciting at 488 nm and collecting at 520 nm (ii) Acceptor channel by exciting at 488 nm and collecting at 669 nm.

Cross talk and bleed-through are measured with donor only and acceptor only samples and found to be negligible for Alexa 488-647 pair. Auto-fluorescence is measured on unlabeled cells. All the images are then background subtracted taking mean intensity of the cytoplasm and Donor and acceptor images are co-localized and endosomes showing co localization are analysed using Image J. Total intensity as well as mean intensity in each endosome is measured in donor and acceptor channels and a ratio of donor to acceptor intensities (D/A) of each endosomes is obtained.

DISCUSSION

The present design of the Nucleic Acid Assembly uses an i-motif forming C-rich sequence that exists as a mismatched duplex at basic pH, folds into an intramolecular i-motif at acidic pH and possesses distinct advantages over the prototype device. Notably, the kinetics of folding, which proves to be rate determining for the response times of the prototype sensor, is dramatically improved. Thus the response times of the new DNA sensors reach as fast as ~15 sec, predisposing them to investigating a greater breadth of cellular applications related to pH maps that correlate with the functional status of the cell.

The main advantage of such rationally designed DNA devices in pH sensing is its predisposition to predictably tuning its pH active regime by altering the pH responsive sequence element that in turn alters i-motif stability. This yields a range of quick response Nucleic Acid Assembly sensors that show transition pH values ranging from 6.3 to 7.3, which in turn enables accurate pH measurements in pH regime pH 5 to pH 7.5.

An additional feature of this design is the presence of a 35 base pair duplex that plays a dual role. One of these is to keep the functional pH responsive C-rich region and its partially complementary strand together even in acidic pH environments. The other is to act as a recognizable epitope for an artificial receptor that is generalizable to the complete range of pH sensors described in this study. This recognizable epitope or 'handle' domain of the DNA pH sensor gains importance in the context of a general strategy that enables small molecule sensing to yield intra-compartmental spatiotemporal chemical maps within living cells.

The Nucleic Acid Assembly alone binds to scavenger receptors and maps spatiotemporal pH changes in endosomes along this pathway. Its use is expanded to more endocytic pathways by functionalizing the Nucleic Acid Assembly with endocytic ligands and mapping pH changes along pathways of the corresponding receptors to those ligands.

However, in the case of endocytic pathways where the ligands are not amenable to conjugation, or trafficking pathways for which no ligands exist, pH variations are still inaccessible. Thus a ligand free method to specifically traffic a DNA pH sensor is generalizable to the largest number of trafficking pathways. This is achieved by fusing a sequence specific DNA binding protein or adapter such as the scFv onto the cellular membrane protein of interest. Using phage display, a collection of recombinant antibodies including one that binds this handle domain at $d(AT)_4$ with a $K_D$~50-80 nM is produced.

In addition, the sequence of hypervariable regions of the recombinant antibodies of the present disclosure yields key indicators of molecular interactions between the DNA epitope and its sequence-specific antibody. Due to its monomeric nature and small size, this scFv acts as an artificial receptor for all DNA pH sensors that incorporate the handle domain. By expressing this scFv as a fusion protein with the membrane protein of interest, it is used as an artificial receptor to recruit a DNA pH sensor enabling one to understand pH correlates of any receptor/protein whose trafficking in endosomal maturation is unknown.

Due to the sequence specificity of the scFv described here, this method is also extendable to the delivery and trafficking of any DNA nanostructure inside cells that incorporate the minimal dsDNA tag i.e. $d(AT)_4$. It is noteworthy that a single phage display screen yields a collection of binders of various binding specificities and affinities from which optimal solutions for various applications are picked. The receptor design strategy is thus not only applicable to any DNA tag—and other chemical entities—but also highly efficient in simultaneously generating a versatile array of DNA device binders/receptors.

As a proof of concept, the scFv is fused to the cytoplasmic tail of Furin whose retrograde endocytosis is characterized in various cell lines. The scFv-Furin chimera is expressed well in HeLa cells and recapitulates the maturation of endogenous Furin. It is predominantly resident in TGN and transported to the plasma membrane through the secretory pathway as seen with endogenous Furin also. During its retrograde transport, scFv-Furin recognizes the Nucleic Acid Assembly present in the culture medium and efficiently endocytoses the latter. Such trafficking of the Nucleic Acid Assembly is not observed in the absence of the scFv domain indicating that the scFv acts as an artificial protein receptor specific for the Nucleic Acid Assembly allowing the DNA sensor to access specifically those compartments associated with its retrograde transport.

Importantly it is seen that scFv-Furin expressed in cells could only recognize and traffic dsDNA that contained an 8 base pair DNA tag corresponding to $d(AT)_4$ as revealed by the competition assay in the presence of excess of $I^{comp}$ and in the presence of excess random dsDNA ($I^{non\ comp}$) This confirms that trafficking of the DNA pH sensor is specific to both scFv and the DNA sequence.

Although Furin is a well known protease, pH correlates of retrogradely transported Furin in endocytic compartments has not been mapped. These are followed by live cell pH measurements on scFv-Furin expressing HeLa cells and labeling the resulting compartments with $I^4_{A488/647}$. Retrogradely trafficking Furin enters the sorting endosome at 5 min which later matures into late endosome over 1 hour, where there is a concomitant acidification of luminal pH. The Nucleic Acid Assembly efficiently captures this maturation from sorting endosomes to late endosomes when following multiple compartments labeled at a given time point, and imaged as a function of time. This reveals that scFv-Furin containing early endosome shows a mildly acidic pH of 6.4±0.33 which is characteristic of sorting endosomal pH. On the other hand, late endosomes containing scFv-Furin show much more acidic pH of 5.4±0.45.

In a complementary method that labels the set of all scFv-Furin containing retrogradely trafficked compartments carried out by a steady-state labeling method, a spatial correlate of compartmental pH for this pathway is obtained. Such a pH map reveals the existence of spatial gradient of compartments with different acidities with a cluster of high pH compartments surrounded by compartments of progressively decreasing pH in retrogradely transported scFvFurin.

The use of a set of high performance DNA based pH sensors and their applications related to being able to exquisitely position them in a well defined intracellular environment is described in the instant disclosure. Importantly, a molecular technology that generalizes the application of DNA sensors to investigate a wide variety of intracellularly trafficking proteins by using a recombinant antibody (scFv) that acts as an artificial receptor is presented. This receptor, the scFv, binds to an 8 base pair dsDNA tag $d(AT)_4$ with nanomolar affinity and allows the label free recognition and positioning of a DNA sensor within endocytic compartments of a cell. This is used as a strategy to target any DNA nanoarchitecture with an associated $d(AT)_4$ tag in cellulo or in vivo.

Importantly, the recognition of DNA nanodevices by this artificial receptor does not compromise nanodevice functionality. This is revealed by the spatiotemporal pH maps obtained post recognition and post delivery within cells. Such measure of intracellular chemistry need not be restricted to pH. This molecular technology is generalizable to the chemical diversity of small molecule sensing, already available to DNA scaffolds that enables the visualization of functionally richer chemical maps of living cells.

The advantages of the Nucleic Acid Assembly (NAA) used in the present disclosure over the conventionally known I-Switch are:

The Nucleic Acid Assembly of the present disclosure has a faster Response time of about 14 seconds as compared to the conventional I-Switch that presently has a Response time of about 180 seconds.

The Nucleic Acid Assembly of the present disclosure has a higher dynamic range and varying $pH_{st}$ as compared to the conventional I-Switch that has less resolution in pH profile in 5-5.8 range (~1.6 fold).

The Nucleic Acid Assembly of the present disclosure is a user modulable and dimeric I-Switch as compared to the conventional I-Switch that has less flexibility due to ternary nature of the complex as well as the $pH_{st}$.

The Nucleic Acid Assembly of the present disclosure has a novel targeting strategy and Biotin-SA conjugation allows any membrane protein to be investigated, as compared to the conventional I-Switch that has conjugation as the strategy and thus only purified proteins, which are conjugatable, are investigated.

In an embodiment of the present disclosure, FIGS. 17(*a*) and (*b*); and FIGS. 18(*a*) and (*b*) give a graphical representation of the comparative analysis between the Nucleic acid assembly of the present disclosure and the conventionally known I-Switch.

We claim:

1. A nucleic acid assembly (NAA) comprising sensor domain and handle domain, optionally along with sensor molecule; wherein the nucleic acid assembly is a duplex selected from the group consisting of SEQ ID Nos. 1 and 4, SEQ ID Nos. 2 and 4, SEQ ID Nos. 3 and 4, SEQ ID Nos. 5 and 6, SEQ ID Nos. 7 and 8, SEQ ID Nos. 9 and 12, SEQ ID Nos. 10 and 12, and SEQ ID No.s 11 and 12.

2. An assembly interfaceable motif (AIM) comprising intracellular targeting motif (ITM) conjugated with an artificial receptor; wherein the artificial receptor is selected from the group consisting of single chain variable fragment (scFv), transcription factor, Zn-fmgered protein, leucine zipper, DNA binding immunoglobulin, DNA binding protein and any combinations thereof and wherein the artificial receptor binds to handle domain of nucleic acid assembly (NAA) as claimed in claim 1.

3. An assembly interfaceable motif (AIM)-nucleic acid assembly (NAA) complex, wherein the nucleic acid assembly as claimed in claim 1 is conjugated with the assembly interfaceable motif (AIM) as claimed in claim 2 through the artificial receptor.

4. A vector comprising assembly interfaceable motif (AIM) as claimed in claim 2, optionally along with intracellular targeting motif (ITM).

5. A cell comprising vector expressing assembly interfaceable motif (AIM) as claimed in claim 2, optionally along with intracellular targeting motif (ITM).

6. A method for obtaining nucleic acid assembly comprising sensor domain and handle domain, optionally along with sensor molecule, wherein the nucleic acid assembly is a duplex selected from group consisting of SEQ ID Nos. 1 and 4, SEQ ID Nos. 2 and 4, SEQ ID Nos. 3 and 4, SEQ ID Nos. 5 and 6, SEQ ID Nos. 7 and 8, SEQ ID Nos. 9 and 12, SEQ ID Nos. 10 and 12, and SEQ ID Nos. 11 and 12, said method comprising acts of:
 a) designing complementary strands coding for sensor domain and handle domain;
 b) positioning and annealing of the complementary strands in solution to obtain the nucleic acid assembly; and
 c) optionally adding the sensor molecule to the Nucleic acid assembly.

7. A method of obtaining nucleic acid assembly [NAA]-assembly interfaceable motif [AIM] complex as claimed in claim 3, said method comprising acts of:
 a) obtaining nucleic acid assembly by method as claimed in claim 6;
 b) obtaining a vector comprising assembly interfaceable motif (AIM);
 c) transfecting a cell with the vector to express the assembly interfaceable motif (AIM) and obtain the AIM on the transfected cell; and
 d) incubating the nucleic acid assembly with the cell comprising the AIM to obtain the nucleic acid assembly [NAA]-assembly interfaceable motif [AIM] complex.

8. A method of intracellular targeting of Nucleic acid assembly-Assembly interfaceable motif (AIM-NAA) complex as claimed in claim 3, said method comprising acts of:
 a) obtaining nucleic acid assembly by method as claimed in claim 6;
 b) obtaining a vector comprising assembly interfaceable motif (AIM);
 c) transfecting a cell with the vector to express the assembly interfaceable motif (AIM) and obtain the AIM on the transfected cell;
 d) incubating the nucleic acid assembly with the cell comprising the AIM for obtaining the nucleic acid assembly [NAA]-assembly interfaceable motif [AIM] complex on the cell; and
 e) re-incubating the complex for cellular uptake and intracellular targeting of the Nucleic acid assembly-Assembly interfaceable motif (AIM-NAA) complex.

9. The nucleic acid assembly as claimed in claim 1, the AIM-NAA complex as claimed in claim 3 and the methods as claimed in claims 6 to 8, wherein the sensor molecule of the NAA is selected from the group consisting of physiological sensor, small molecule sensor, organic molecules, proteins, nucleic acids, metabolites, drugs and their derivatives, amino acids, nucleotides and its derivatives, biological cofactors, antibiotics, vitamins, proteins, small peptides, toxins, lipids, growth factors, hormones and enzymes and any combinations thereof.

10. The AIM as claimed in claim 2, the AIM-NAA complex as claimed in claim 3, the vector as claimed in claim 4, the cell as claimed in claim 5 and the methods as claimed in claims 7 and 8, wherein the AIM is selected from group consisting of nucleic acid binding protein, recombinant antibody, transcription factor, Zn-finger protein, leucine zipper, peptide, proteins that possess natural receptor, trafficking protein, toxins, virus, viral coat protein, cell penetrating peptide, signal sequence, intracellular targeting sequence, small organic molecule, endocytic ligand, enzyme, aptamer against trafficking protein and any combinations thereof.

11. The AIM as claimed in claim 2, the AIM-NAA complex as claimed in claim 3, the vector as claimed in claim 4, the cell as claimed in claim 5, wherein the ITM is selected from the group consisting of endocytosable plasma membrane protein, protein that possesses a natural receptor, trafficking protein, toxins, virus, viral coat protein, cell penetrating peptide, signal sequence, intracellular targeting sequence, small organic molecule and endocytic ligand or any combinations thereof; and the artificial receptor is selected from group comprising single chain variable fragment (scFv), transcription factor, Zn-fingered protein, leucine zipper, DNA binding immunoglobulin, DNA binding protein and any combinations thereof.

12. The AIM as claimed in claim 2, the AIM-NAA complex as claimed in claim 3, the vector as claimed in claim 4, the cell as claimed in claim 5, wherein the ITM is Furin and binds to nucleic acid assembly (NAA) by way of hydrogen bonding interactions.

13. The vector as claimed in claim 4, the cell as claimed in claim 5 and the methods as claimed in claims 7 and 8, wherein the vector is selected from the group consisting of plasmids, viruses, or viral vectors, cosmids, phagemids and artificial chromosomes.

14. The cell as claimed in claim 5 and the methods as claimed in claims 7 and 8, wherein the cell is eukaryotic cell and is selected from the group consisting of HeLa cell, TRVb-1 and IA2.2 cell.

15. The methods as claimed in claims 7 and 8, wherein the incubating is carried out at temperature ranging from about 4° C. to about 37° C.

16. The method as claimed in claim 8, wherein the re-incubating is carried out at temperature ranging from about 20° C. to about 37° C.; and the intracellular targeting is to endosome.

17. A kit for obtaining nucleic acid assembly [NAA]-assembly interfaceable motif [AIM] complex, said kit comprising components selected from the group consisting of nucleic acid assembly of claim 1, AIM as claimed in claim 2, vector as claimed in claim 4, cell as claimed in claim 5 and instruction manual and any combinations thereof.

18. A method of assembling a kit as claimed in claim 17, said method comprising act of combining components selected from group consisting of nucleic acid assembly of claim 1, AIM as claimed in claim 2, vector as claimed in claim 4, cell as claimed in claim 5, instruction manual and any combinations thereof.

19. A kit for intracellular targeting of nucleic acid assembly [NAA]-assembly interfaceable motif [AIM] complex, said kit comprising components selected from the group consisting of nucleic acid assembly of claim 1, AIM as claimed in claim 2, nucleic acid assembly [NAA]-assembly interfaceable motif [AIM] complex as claimed in claim 3, vector as claimed in claim 4, cell as claimed in claim 5 and instruction manual and any combinations thereof.

20. A method of assembling a kit as claimed in claim 19, said method comprising act of combining components selected from the group consisting of nucleic acid assembly of claim 1, AIM as claimed in claim 2, nucleic acid assembly [NAA]-assembly interfaceable motif [AIM] complex as claimed in claim 3, vector as claimed in claim 4, cell as claimed in claim 5 and instruction manual and any combinations thereof.

* * * * *